(12) United States Patent
Chavan

(10) Patent No.: US 8,778,336 B2
(45) Date of Patent: Jul. 15, 2014

(54) STABILIZED PROTEASES THAT HAVE BEEN IMMOBILIZED AND FURTHER CROSSLINKED FOR USE IN SKIN CARE

(75) Inventor: Manasi Chavan, Stony Brook, NY (US)

(73) Assignee: BASF Corporation, Florham Park, NJ (US)

(*) Notice: Subject to any disclaimer, the term of this patent is extended or adjusted under 35 U.S.C. 154(b) by 148 days.

(21) Appl. No.: 13/009,825

(22) Filed: Jan. 19, 2011

(65) Prior Publication Data

US 2011/0177052 A1    Jul. 21, 2011

Related U.S. Application Data

(60) Provisional application No. 61/296,052, filed on Jan. 19, 2010.

(51) Int. Cl.
| | | |
|---|---|---|
| A61K 8/66 | (2006.01) | |
| A61Q 19/08 | (2006.01) | |
| A61K 38/48 | (2006.01) | |
| A61K 47/48 | (2006.01) | |
| C12N 9/96 | (2006.01) | |

(52) U.S. Cl.
CPC ............ *A61K 8/66* (2013.01); *A61K 47/48176* (2013.01); *A61K 38/4873* (2013.01); *C12Y 304/22002* (2013.01); *A61Q 19/08* (2013.01); *C12N 9/96* (2013.01); *A61K 2800/57* (2013.01)
USPC ............................ 424/94.3; 435/188; 435/212

(58) Field of Classification Search
CPC ............. A61K 8/66; A61K 47/48176; A61K 38/4873; A61K 2800/57; A61K 38/488; A61K 38/482; A61K 38/48; A61K 8/733; A61Q 19/08; A61Q 19/00; C12N 9/96
See application file for complete search history.

(56) References Cited

U.S. PATENT DOCUMENTS

| | | | |
|---|---|---|---|
| 5,961,990 A | 10/1999 | Delrieu et al. | |
| 6,319,507 B1 | 11/2001 | Delrieu et al. | |
| 6,416,769 B1 | 7/2002 | Vromen | |
| 6,607,714 B1 | 8/2003 | Dupuis et al. | |
| 7,241,456 B2 | 7/2007 | Vromen | |
| 7,311,926 B2 | 12/2007 | Grate et al. | |

(Continued)

FOREIGN PATENT DOCUMENTS

| | | |
|---|---|---|
| CN | 101396328 A | 4/2009 |
| IN | 200700151 | 10/2008 |

(Continued)

OTHER PUBLICATIONS

Kim "Highly stable trypsin-aggregate coatings on polymer nanofibers for repeated protein digestion" Proteomics 2009, 9, Available Mar. 13, 2009, 1893-1900.*

(Continued)

*Primary Examiner* — Blaine Lankford
*Assistant Examiner* — Charles Zoltan Constantine
(74) *Attorney, Agent, or Firm* — Shiela A. Loggins

(57) ABSTRACT

Disclosed is an invention which relates to synthesizing immobilized and crosslinked proteases derived from plants for use as skin care agents. The resulting stabilized protease will minimally penetrate the skin because of its immobilized nature. It will retain activity because of its crosslinked nature and, in certain embodiments, due to its stabilization via physical additives. The present invention relates in particular to a linked papain product used in topical skin applications.

21 Claims, 23 Drawing Sheets

(56) References Cited

U.S. PATENT DOCUMENTS

| | | |
|---|---|---|
| 7,416,869 B2 | 8/2008 | Guth et al. |
| 2002/0086042 A1 | 7/2002 | Delrieu et al. |
| 2004/0108608 A1 | 6/2004 | Ju Hee et al. |
| 2004/0120917 A1 | 6/2004 | Perrier et al. |
| 2004/0228831 A1 | 11/2004 | Belinka et al. |
| 2005/0013925 A1 | 1/2005 | Cabey et al. |
| 2005/0281795 A1 | 12/2005 | Jolly |
| 2006/0210500 A1* | 9/2006 | Bicard-Benhamou et al. . 424/63 |
| 2006/0233783 A1 | 10/2006 | Gomez |
| 2007/0071711 A1 | 3/2007 | Vromen |
| 2007/0148119 A1 | 6/2007 | Guth et al. |
| 2008/0020036 A1 | 1/2008 | Jolly |
| 2009/0291133 A1 | 11/2009 | Wang et al. |

FOREIGN PATENT DOCUMENTS

| | | |
|---|---|---|
| KR | 804096 | 2/2008 |
| MX | 2002 002010 | 8/2003 |
| WO | 91/06287 A1 | 5/1991 |
| WO | 92/03543 A1 | 3/1992 |
| WO | 2004110358 A2 | 12/2004 |
| WO | 2005010086 A2 | 2/2005 |
| WO | 2005034886 A1 | 4/2005 |
| WO | 2005110503 A1 | 11/2005 |

OTHER PUBLICATIONS

Geitmann "Studies of substrate-induced conformational changes in human cytomegalovirus protease using optical biosensor technology" Analytical Biochemistry, 2004, 332, 203-214.*
Centerchem "Diocide", 2008, CenterChem Inc, Norwalk CT, available at www.centerchem.com/PDFs/DIOCIDE%20Tech%20Lit%200808.pdf.*
English language abstract of CN 101396328 printed on Apr. 19, 2011 from Espacenet.com.
English language abstract of WO 2005/034886 printed on Apr. 19, 2011 from Espacenet.com.
Chemical Abstract AN 2008:1203217 of IN 200700151.
Chemical Abstract AN 2008:325777 of KR 804096.
Chemical Abstract AN 2007:797877 of MX 2002 002010.
Royer et al.; "Cross-Linking of Reversibly Immobilized Enzymes"; Department of Biochemistry, The Ohio State University; Aug. 1977; vol. 80 No. 1; pp. 89-94.
Anwar T et al: "Cross-linked stem bromelain: A more stabilized active preparation", Biocatalysis and Biotransformation, Harwood Academic Publ., Basel, CH, vol. 25, No. 6 Nov. 1, 2007, pp. 453-458, XP009170404, ISSN: 1024-2422, DOI: 10.1080/102420701568575.
EP Search Report dated Jul. 3, 2013.
International Search Report dated Oct. 20, 2011.

* cited by examiner

STABILIZED PROTEASES THAT HAVE BEEN IMMOBILIZED AND FURTHER CROSSLINKED FOR USE IN SKIN CARE

PRIORITY

This application claims priority to U.S. Provisional Application No. 61/296,052, filed Jan. 19, 2010.

SUMMARY

Disclosed is an invention which relates to synthesizing immobilized and crosslinked proteases derived from plants for use as skin care agents. The resulting stabilized protease will minimally penetrate the skin because of its immobilized nature. It will retain activity because of its crosslinked nature and, in certain embodiments, due to its stabilization via physical additives. The present invention relates in particular to a linked papain product used in topical skin applications.

BACKGROUND

The activity of proteases is important in epidermal homeostasis. Thus, proteases have various potential benefits when applied to the skin, but are subject to certain limitations. Papain is a powerful protease derived from papaya and certain other plants. However, it loses activity rapidly in a solution state. This is because papain, similar to all proteases, digests itself as well as undergoes denaturation. In addition, other difficulties with conventional papain products may be encountered when these papain products are used as topical skin care agents in connection with skin penetration and skin irritation. It is highly desirable to develop protease products, and more particularly, a papain product, for use in skin care which do not have such limitations.

To overcome the above-mentioned difficulties in the conventional art, exemplary embodiments of the present invention provide a modified stable crosslinked protease product via the techniques set forth described herein, and particularly a modified stable crosslinked protease product.

For example, in some embodiments of the present invention, in order to obtain a stable crosslinked papain product, papain is immobilized on a polymer like, for example, a carbomer or carbopol in a primary cross-linking reaction and then a secondary crosslinking reaction is subsequently performed by adding a homobifunctional crosslinking reagent of low molecular weight which is amine reactive such as, for example, Dimethyl adipimidate (DMA), Bis(Sulfosuccinimidyl) suberate (BS3), Dimethyl Suberimidate (DMS), Dimethyl pimelimidate (DMP) and Disuccinimidyl suberate (DSS).

In other exemplary embodiments of the present invention, the primary crosslinking reaction and the secondary crosslinking reaction are performed to obtain a stable crosslinked papain product and then the stable crosslinked papain is further stabilized using physical stabilizers such as, for example, sugars or sugar polymers. For example, sodium alginate may be used as a physical stabilizer in accordance with exemplary embodiments of the present invention.

The above crosslinked stabilized papain product may still even be further stabilized by including the above stabilized papain product in certain preservative systems or an oil in water formulation.

The benefits of the immobilized, crosslinked and stabilized protease (e.g. papain) complex according to exemplary embodiments of the present invention include but are not limited to:
1) minimal skin penetration,
2) retention of proteasic activity in solution or dry form
3) minimal skin irritation, and
4) ease of formulation In still other embodiments of the present invention, cosmetic, personal care, and pharmaceutical compositions comprising stabilized proteases are described.

BRIEF DESCRIPTION OF THE FIGURES

The following figures are presented for the purposes of illustration only, and are not intended to be limiting.

DETAILED DESCRIPTION

Figure 1:
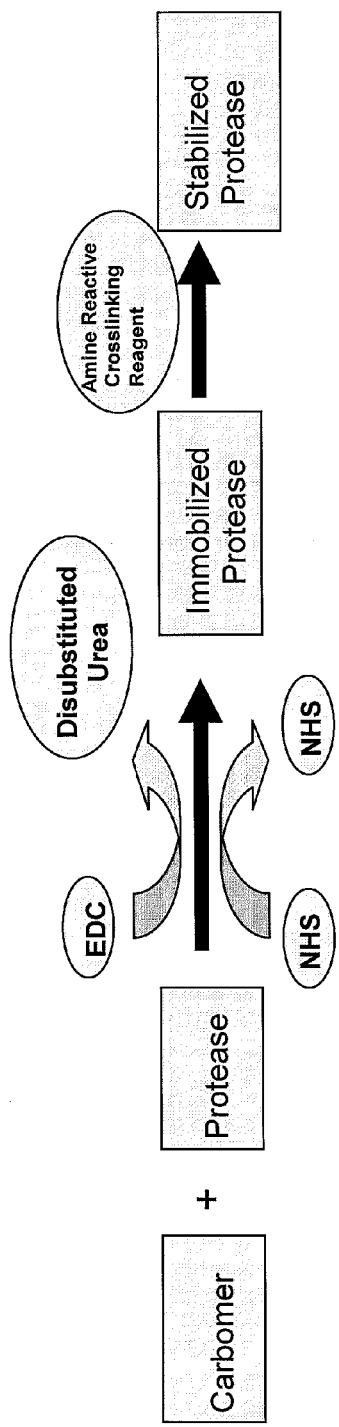
FIG. 1 illustrates crosslinking reactions for forming a stable crosslinked protease in accordance with the present invention.

Unless otherwise defined, all technical and scientific terms used herein have the same meaning as commonly understood by one of ordinary skill in the art of which this invention belongs. Although methods and materials similar to or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims. As will be apparent to one of skill in the art, specific features and embodiments described herein can be combined with any other feature or embodiment.

The epidermis is comprised of several strata or layers. The outermost layer, the Stratum corneum, is made up of dead cells which have migrated upward over the course of several days from the strata below. These dead cells are normally shed from the surface of the skin via a process called epidermal desquamation which stimulates growth of newer cells at a deeper level. Younger skin is more efficient at this process than aged or damaged skin. As a result, aged skin appears dull, thick and less toned. This may be exacerbated by environmental factors, such as exposure to sunlight; hormonal influences, such as androgens, estrogens, and epidermal growth factor; and vitamin deficiencies, such as deficiencies in vitamins A and D. Protease activity is a key factor in the desquamation process. Thus, the application of proteases to the skin for cosmetic effects, such as skin smoothing and anti-aging, is desirable. However, use of proteases in cosmetic and other applications is known to have three major limitations: instability, potential for allergenicity, and skin penetration.

The invention is based, at least in part, on the discovery that proteases can be stabilized through certain crosslinking reactions to form a protease carbomer copolymer, also referred to herein as a "stabilized" protease. Such stabilized proteases comprise a protease crosslinked to a carbomer, wherein the primary amines of the protease are crosslinked to the carboxyl groups of the carbomer and wherein the amines of the protease are further crosslinked by an amine reactive crosslinking agent. In one embodiment of the invention, the stabilized protease further comprises a physical stabilizer, for example a sugar or sugar polymer.

A method of forming such stabilized protease product is also disclosed wherein a primary crosslinking reaction is performed to crosslink the primary amines of the protease to the carboxyl groups of a carbomer and a secondary crosslinking reaction is performed via an amine reactive crosslinking reagent.

Proteases

Proteases are enzymes which catalyse the breakdown of proteins. Proteases, being proteins themselves, have a tendency to undergo autodegradation and are unstable in nature. This proteinaceous nature also renders them allergenic. Additionally, because of their ability to degrade proteins, they may penetrate to the deeper layers of the epidermis and cause damage to the underlying strata. Suitable proteases for use in the present invention include papain, ficin, bromelain, and actinidain.

Ficin is a nonspecific sulfhydryl protease isolated from the latex of the fig, the fruit of the *Ficus* tree. Ficin is most commonly obtained from *Ficus carica* and *Ficus glabatra*. However, ficin may also be isolated from the fruits of other *Ficus* species, such as *Ficus elastica* and *Ficus insipida*. Bromelain is a sulfhydryl protease isolated from the stem and/or fruit of the pineapple (*Ananas comosus*). Actinidain, also known as actinidin is a cysteine protease obtained from the kiwi fruit (*Actinidia deliciosa*). Papain is a cysteine protease obtained from papaya (*Carcia papaya*) and mountain papaya (*Vasconcellea cundinamarcensis*), most often from the latex of the green, unripe fruit. The proteases are present in a concentration between about 0.1% and 5% by weight.

Carbomers

The protease is first immobilized on a carbomer. Carbomers are homopolymers of acrylic acid having a high molecular weight which is crosslinked with any of several polyalcohol allyl ethers (e.g., allyl ether pentaerythritol, allyl ether of sucrose, or allyl ether of propylene). Examples of suitable carbomers are Carbomer 910, Carbomer 934, Carbomer 934p, Carbomer 940, and Carbomer 941, wherein the numberical suffix indicates the average molecular weight of the polymer chains. As used herein, an "immobilized" protease or "linked" protease refers to a protease that has been reacted with the carbomer via the primary crosslinking reaction. Suitable crosslinking reagents for this primary crosslinking reaction are reagents capable of coupling carboxyl groups to primary amines. One example of a suitable crosslinking reagent is the water soluble carbodiimide 1-ethyl-3-(3-dimethyl aminopropyl)carbodiimide. EDC is a zero-length cross-linking agent used to couple carboxyl groups to primary amines. EDC reacts with a carboxylic acid groups to give O-acylisourea groups, which form cross-links after reaction with free amine groups. EDC is a primary cross-linker in this embodiment which gets converted to a disubstituted urea during the course of the reaction. The NHS is an acid ester and a catalyst which increases the rate of the cross-linking and remains unchanged during the cross-linking reaction.

Chemical Crosslinkers

Once immobilized on the carbomer, the immobilized protease is reacted with an amine reactive crosslinking reagent in a secondary crosslinking reaction to form a protease carbomer copolymer, also referred to herein as a "stabilized protease". The crosslinking reagent is preferably a low molecular weight crosslinker such that the crosslinker will completely react or nearly completely react in the secondary crosslinking reaction. Examples of suitable crosslinkers that can be used include imidoester crosslinkers such as dimethyl adipimidate (DMA), dimethyl pimelimidate (DMP), dimethyl suberimidate (DMS), dimethyl 3,3 dithiobis. The amine reactive crosslinkers may be provided in various concentrations ranging from about 0.05% to about 5% by weight, preferably between about 1% and 5%. In certain embodiments, DMA is utilized.

Physical Stabilizers

After chemical crosslinking, the immobilized and crosslinked protease is optionally further stabilized with a physical stabilizer, for example sugar or sugar polymers. Examples of suitable sugars or sugar polymers are sodium alginate, trehalose, mannitol, glycerol, and Xanthan. In one embodiment, sodium alginate is utilized. Such physical stabilizers may be included in concentrations between about 0.1% and 5% by weight.

Figure 2:
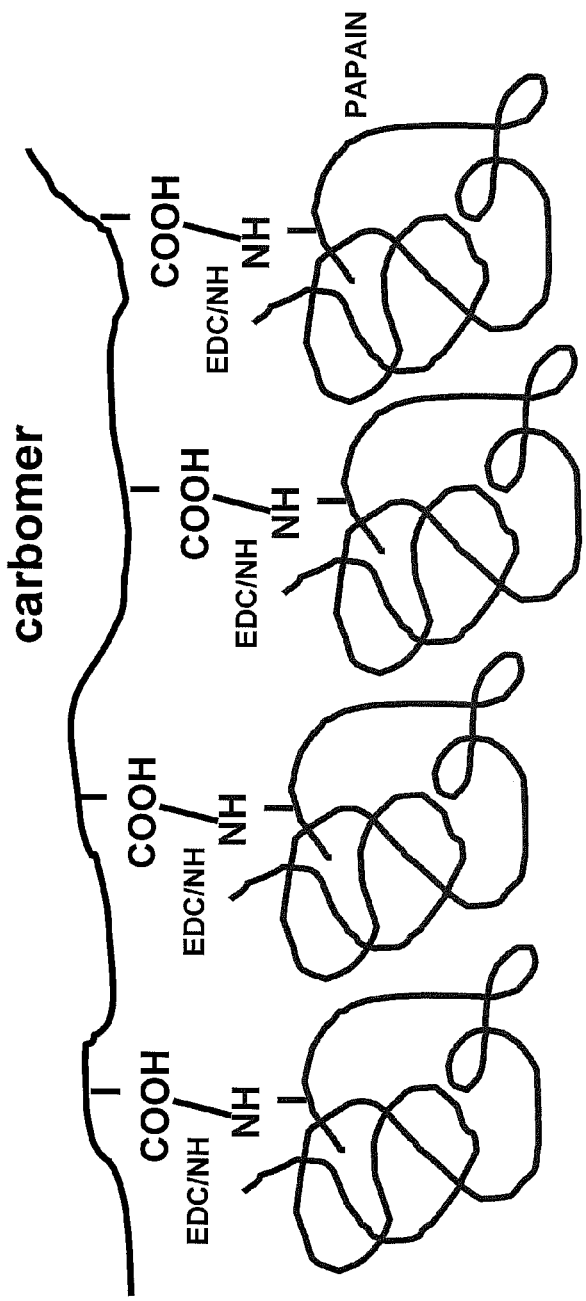
FIG. 2 illustrates a stable crosslinked papain product in accordance with an exemplary embodiment of the present invention which has undergone the crosslinking reactions illustrated in FIG. 1.

An illustration of crosslinking reaction for forming one embodiment of the stabilized proteases of the present invention is are shown in FIG. 1. An illustration of a stabilized papain product is shown in FIG. 2.

Applications/Formulations

Stabilized proteases of the present invention have miminal skin pentetration, retain proteasic activity in solution or dry form, have minimal skin irritation, and are relatively easy to provide in a formulation. Accordingly, exemplary embodiments of the present invention provide a more stable and much safer protease products in comparison to the protease products of the conventional art, particularly stabilized papain products embodiments.

Stabilized proteases are suitable for use in cosmetic and personal care formulations, for example, exfoliating preparations, anti-wrinkle and/or anti-aging preparations, bath additives, hair care preparations, liquid and sold soaps, cleansing solutions, moist cleansing cloths, oils or powders, anti-acne preparations. Stabilized proteases are particularly suitable for treating dry, aged or damaged skin by applying one or more of the stabilized proteases of the present invention to dry, aged or damaged skin in need of treatment.

Cosmetic and/or personal care formulations may be in the form, for example, of water-in-oil or oil-in-water emulsion, an alcoholic or alcohol containing formulation, a vesicular dispersion of an ionic or non-ionic amphiphilic lipid, or a gel. Exemplary cosmetic and/or personal care formulations comprise between about 0.5% and 5% stabilized protease, by weight, preferably between about 1% and 3%.

The stabilized proteases of the present invention are also suitable for pharmaceutical applications, for example, debridement applications. Debridement is the removal of dead or damaged tissue from wounds, for example ulcerative wounds, or burns in order to assist healing. In one embodiment of the invention, one or more of the stabilized proteases of the present invention are applied to skin wounds or burns in need of debridement. Exemplary formulations and products comprising stabilized proteases for treatment of wounds or burns include bandages/dressings, patches, wash solutions, ointments or gels, or synthetic tissues. In certain embodiments, debridement compositions, for example, bandages, dressings or patches, may optionally include antimicrobials. For debridement applications, the amount of stabilized protease included in the pharmaceutical compositions will be an amount which effectively debrides necrotic tissue and liquefies pus in wounds, and which effects removal in a reasonable time (for example, over a seven day period, of substantially all of such materials.

In addition to skin care applications, the stabilized proteases of the present invention may also be suitable in other applications known in the art wherein a stable form of a protease would be desired. One exemplary application is oral care compositions.

Topical compositions comprising stabilized proteases may further comprise a variety of other ingredients that are conventionally used in cosmetic, personal care, or pharmaceutical formulations provided they do not unacceptably alter the benefits of the invention. Nonlimiting examples of optional conventional ingredient classes include fragrances, pigments, colorings/colorants, essential oils, astringents, anti-aging agents, anti-acne agents, anti-caking agents, antifoaming agents, antimicrobial agents, antioxidants, binders, pH adjusters, skin bleaching and lightening agents, skin conditioning agents, sunscreens, preservatives, anti-inflammatory agents, moisturizers, thickeners, and vitamins.

For certain embodiments of cosmetic, personal care, and/or pharmaceutical applications, it is desirable to further include a preservative system with the stabilized protease. Enzymes are known to denature under harsh conditions like higher temperatures and the presence of incompatible chemicals like strong emulsifiers. Two example preservative systems suitable for use with stabilized proteins, and particularly suitable for stabilized papain, are:
  (a) Phenoxyethanol+Benzoic acid
  (b) Diocide (Blend of Phenoxythanol+Capryl glycol+ Hexylene Glycol)

EXAMPLES

The invention is further described in the following example, which does not limit the scope of the invention described in the claims.

Example 1

A stable papain product which retains its proteasic activity and is safer than conventional papain products which contain free papain was produced by performing a primary crosslinking reaction in which 1% papain was crosslinked to Carbopol using carbodiimide 1-ethyl-3-(3-dimethyl aminopropyl)carbodiimide hydrochloride (EDC) together with N-hydroxysulfosuccinimide (NHS). Next, a secondary cross-linking reaction was then performed in which the immobilized papain is reacted with dimethyl adipimidate (DMA) to further crosslink the crosslinked papain to thereby form a stable cross-linked papain product. DMA was provided in concentration of 1% and the papain was provided in a concentration of 1% by weight.

Three (3) experimental lab batches of the above stabilized papain product were conducted to determine the effect of 1% of DMA has on the enzyme activity/stability of the primary crosslinked papain over a storage period over 12 weeks. The reaction conditions for performing the experiments are set forth in Table 1.

TABLE 1

| Assay protocol using Invitrogen E6639 EnzChek ® kit for enzyme activity | | | |
|---|---|---|---|
| Papain standard curve | | | |
| STD # | Stock solution(U/mL) | Stock (1 U/mL) | Assay buffer |
| 1 | 1 | 1000 | 0 |
| 2 | 0.5 | 500 | 500 |
| 3 | 0.25 | 250 | 750 |
| 4 | 0.1 | 100 | 900 |
| 5 | 0.05 | 50 | 950 |
| 6 | 0.01 | 10 | 990 |
| 7 | 0.005 | 5 | 995 |
| 8 | 0 | 0 | 1000 |

Prepare 1 Unit/mL stock solution of papain
10 mg Sigma papain
25 ml dl 1× digestion
buffer
Material & buffer requirement:
0.1M Sodium Bicarbonate, pH 8.3
1× Digestion buffer: PBS pH6 + 50 ul of TX-100
1 Mg/ml stock of BODIPY TRX casein =
1 vial of substrate and dissolve in 0.2 ml of Bicarbonate buffer
10 ug/mL working solution of BODIPY casein:
Add 0.2 mL of stock substrate in 19.8 ml of Digestion buffer
in 50 ml falcon TABLE 1-continued Assay protocol using Invitrogen E6639 EnzChek ® kit for enzyme activity

| | |
|---|---|
| Assay: | 20 ul of STD/sample |
| | 80 ul of 1X digestion biffer |
| | 100 ul of 10 ug/mL working solution of BODIPY casein |
| Samples: | 50 ul of linked papain mixed with 150 ul of 1× digestion buffer containing 0.1% Triton X-100 |
| Procedure: | Incubate the plate at room temperature for one hour with moderate agitation. Protect the plate from light. Read the flurescence in a fluorescence microplate reader. Using standard fluorescein filters excitation 530/25 nm, emission 620/40 nm. |

The results of the three separate lab batches for determining the retained activity of immobilized papain with 1% DMA and without DMA at various temperatures over a 12 week period are set forth below in Tables 2(a)-5(b). Table 2(a) depicts the percentage of retained activity of linked immobilized papain in the experimental samples which also contain 1% DMA. Table 2(b) depicts the percentage of retained activity of immobilized papain in the control samples which do not include DMA. The experimental samples and the control samples were essentially the same except that the control samples did not contain any DMA.

TABLE 2(a)

Immobilized Papain crosslinked with 1% DMA

| Time | 4° C. | 25° C. | 40° C. | 50° C. |
|---|---|---|---|---|
| | 100 | 100 | 100 | 100 |
| 2 week | 103.927 | 106.806 | 92.670 | 75.654 |
| 4 week | 101.832 | 98.168 | 69.372 | 26.70 |
| 6 week | 97.906 | 95.812 | 55.236 | 13.089 |
| 0 week | 96.073 | 92.670 | 36.911 | 2.356 |
| 12 week | 95.812 | 84.296 | 12.923 | 2.068 |

TABLE 2(b)

Immobilized Papain (without DMA) - Control

| Time | 4 C. | 25 C. | 40 C. | 50 C. |
|---|---|---|---|---|
| 0 week | 100 | 100 | 100 | 100 |
| 2 week | 96.419 | 68.286 | 53.708 | 25.064 |
| 4 week | 91.049 | 57.545 | 47.826 | 8.440 |
| 6 week | 90.537 | 45.013 | 26.087 | 2.558 |
| 8 week | 85.166 | 27.877 | 12.788 | 0.256 |
| 12 week | 78.772 | 21.043 | 6.115 | 0.305 |

TABLE 3(a)

Immobilized Papain Crosslinked with 1% DMA

| Time | 4 C. | 25 C. | 40 C. | 50 C. |
|---|---|---|---|---|
| 0 week | 100 | 100 | 100 | 100 |
| 2 week | 107.320 | 110.000 | 87.530 | 65.430 |
| 4 week | 95.620 | 92.650 | 65.430 | 29.76 |
| 6 week | 91.420 | 87.210 | 56.540 | 10.430 |
| 8 week | 87.240 | 84.320 | 30.120 | 1.340 |
| 12 week | 85.350 | 80.460 | 10.870 | 1.000 |

TABLE 3(b)

Immobilized Papain (without DMA) - Control

| Time | 4 C. | 25 C. | 40 C. | 50 C. |
|---|---|---|---|---|
| 0 week | 100 | 100 | 100 | 100 |
| 2 week | 92.340 | 63.450 | 62.870 | 20.870 |
| 4 week | 88.010 | 53.450 | 44.620 | 5.670 |
| 6 week | 84.320 | 44.670 | 28.980 | 1.650 |
| 8 week | 81.760 | 22.970 | 10.960 | 0.430 |
| 12 week | 72.350 | 17.650 | 4.300 | 0.010 |

TABLE 4(a)

Immobilized Papain crosslinked with 1% DMA

| Time | 4 C. | 25 C. | 40 C. | 50 C. |
|---|---|---|---|---|
| 0 week | 100 | 100 | 100 | 100 |
| 2 week | 99.000 | 99.980 | 92.670 | 68.520 |
| 4 week | 97.620 | 96.210 | 62.650 | 22.01 |
| 6 week | 96.420 | 92.510 | 52.980 | 10.650 |
| 8 week | 90.610 | 82.100 | 31.000 | 2.420 |
| 12 week | 88.010 | 80.110 | 10.650 | 0.890 |

TABLE 4(b)

Immobilized Papain (without DMA) - Control

| Time | 4 C. | 25 C. | 40 C. | 50 C. |
|---|---|---|---|---|
| 0 week | 100 | 100 | 100 | 100 |
| 2 week | 98.870 | 71.820 | 50.980 | 27.870 |
| 4 week | 86.340 | 52.340 | 41.620 | 5.750 |
| 6 week | 80.730 | 40.210 | 22.320 | 1.230 |
| 8 week | 81.530 | 20.410 | 11.876 | 0.910 |
| 12 week | 75.610 | 15.620 | 3.110 | 0.030 |

TABLE 5(a)

Mean value for % of retained activity of immobilized papain crosslined with 1% DMA of Batch 1 (Table 3), Batch 2 (Table 4) and Batch 3 (Table 5)

| Time | 4 C. | 25 C. | 40 C. | 50 C. |
|---|---|---|---|---|
| 0 week | 100 | 100 | 100 | 100 |
| 2 week | 103.4 | 105.6 | 91.0 | 69.9 |
| 4 week | 98.4 | 95.7 | 65.8 | 26.2 |
| 6 week | 95.2 | 91.8 | 54.9 | 11.4 |
| 8 week | 91.3 | 86.4 | 32.7 | 2.0 |
| 12 week | 89.7 | 81.6 | 11.5 | 1.3 |

TABLE 5(b)

Mean value for % of retained activity of immobilized papain (without DMA) of Batch 1 (Table 3), Batch 2 (Table 4) and Batch 3 (Table 5)

| Time | 4 C. | 25 C. | 40 C. | 50 C. |
|---|---|---|---|---|
| 0 week | 100 | 100 | 100 | 100 |
| 2 week | 95.88 | 67.85 | 55.85 | 55.85 |
| 4 week | 88.47 | 54.44 | 44.69 | 44.69 |
| 6 week | 85.20 | 43.30 | 25.80 | 25.80 |
| 8 week | 82.82 | 23.75 | 11.87 | 11.87 |
| 12 week | 75.58 | 18.10 | 4.51 | 4.51 |

Figure 3:
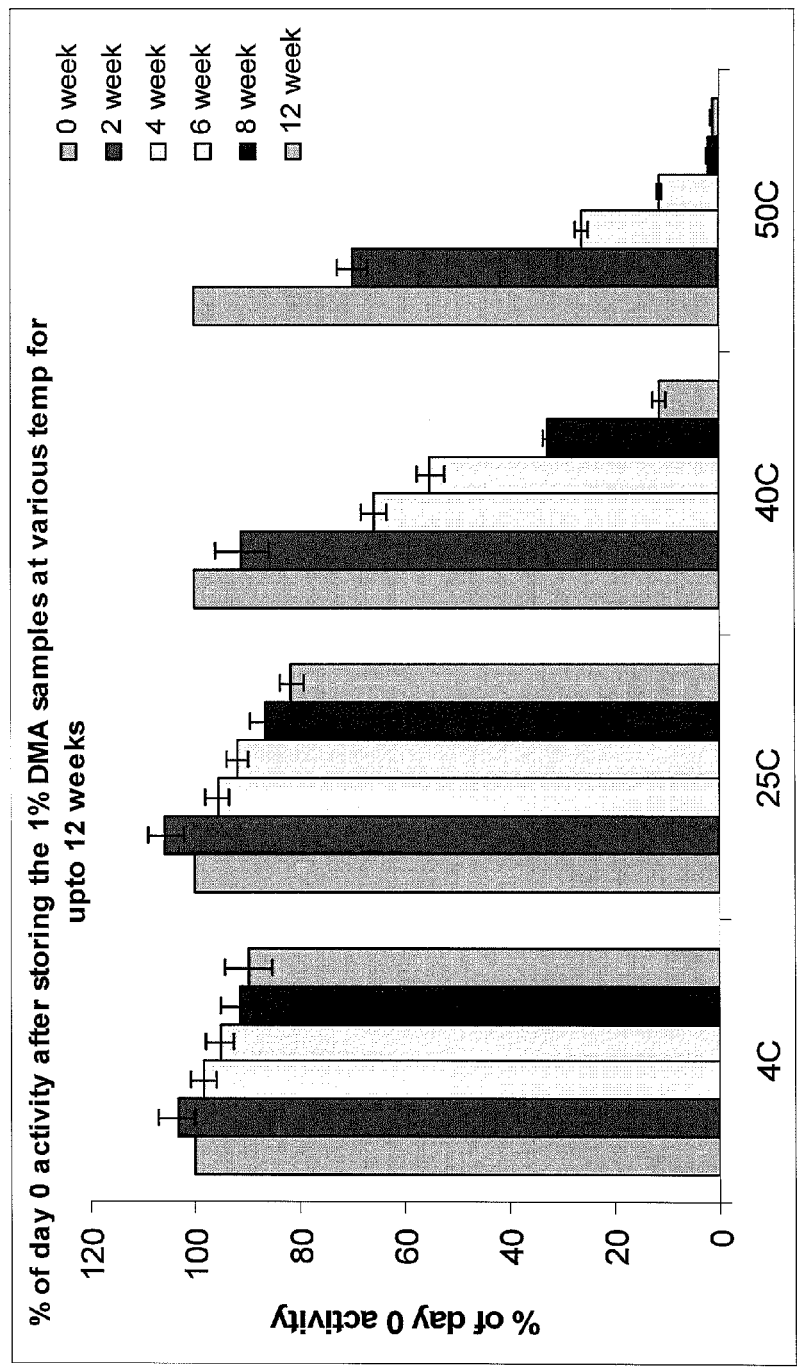
FIG. 3 illustrates the percentage of day 0 activity after storing samples of a stabilized papain in accordance with an exemplary embodiment of the present invention at various temperatures for up to 12 weeks.
Figure 4:
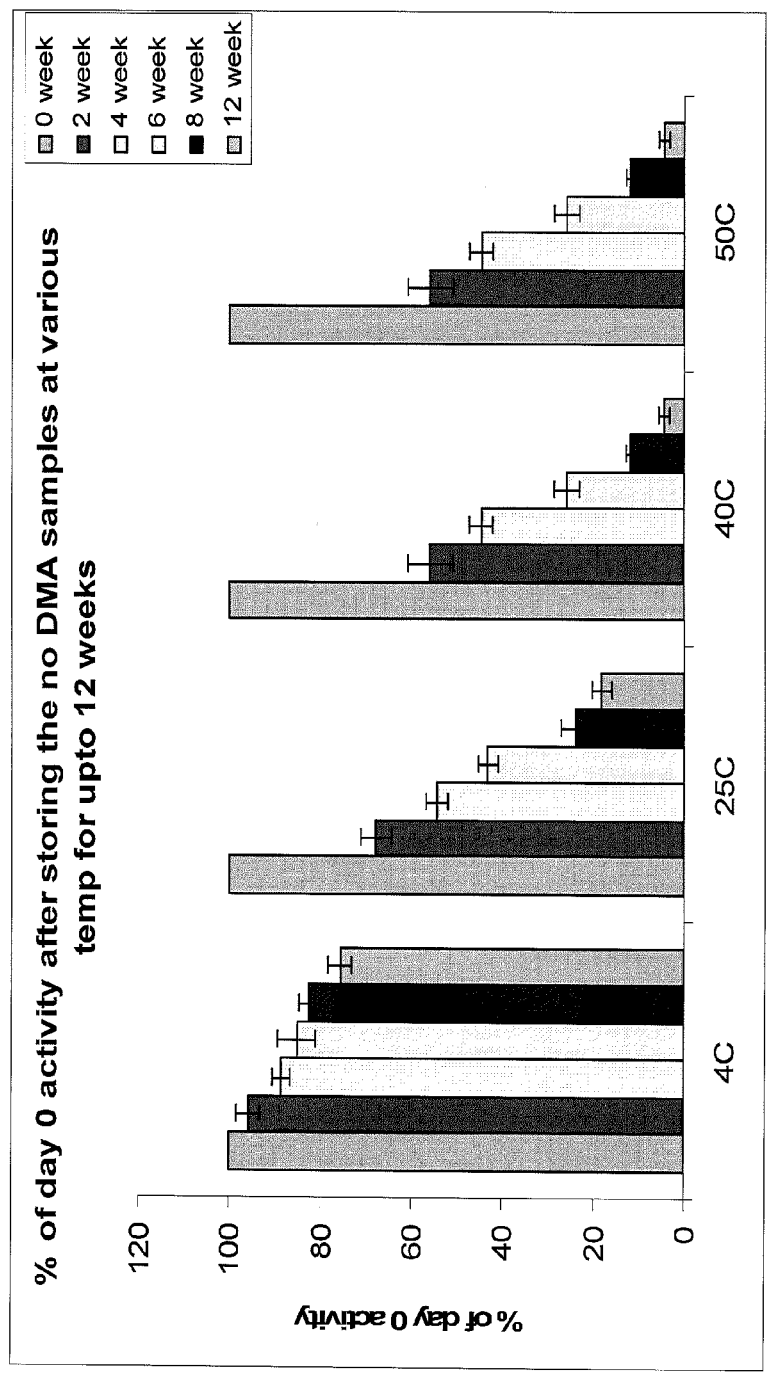
FIG. 4 illustrates the percentage of day 0 activity after storing the no DMA samples at various temperatures for up to 12 weeks.

As can be seen from the results of tables 2(a)-5(b), the activity of immobilized papain which was cross-linked with 1% DMA in the experimental samples was significantly greater over a variety of temperatures than the activity of immobilized papain in the control samples which was not reacted with DMA. Accordingly, papain which has undergone a primary crosslinking reaction to cross-link papain to a carbomer and then undergone a secondary cross-linking reaction with 1% DMA is significantly more stable than control samples of papain which has undergone the primary cross-linking reaction but has not undergone a secondary cross-linking reaction with DMA. Furthermore, FIGS. 3 and 4 illustrate the results of tables 2(a)-5(b) that the activity of immobilized papain which has been crosslinked with 1% DMA is significantly greater over a variety of temperatures than the activity of immobilized papain in the control samples which was not reacted with DMA.

Figure 5:
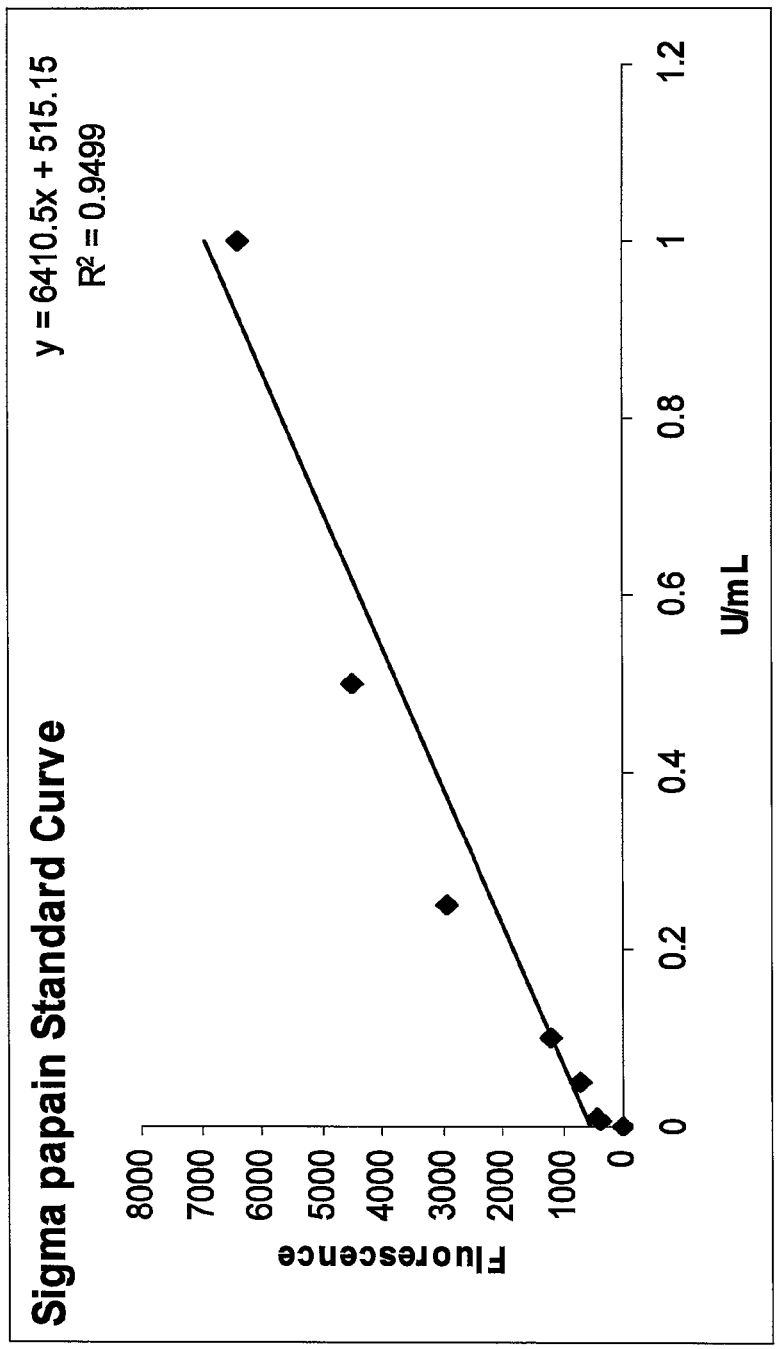
FIG. 5 illustrates a Sigma papain standard curve

As set forth below in Tables 6 and 7, papain activity in the experimental samples and the control samples were determined based upon fluorescence change per unit sample of the immobilized papain. A Sigma papain activity standard curve as shown in FIG. 5 was developed for assistance in quantitating the activity of immobilized papain crosslinked with 1% DMA in accordance with the present example. As noted above, an EnzChek® protease assay kit (E-6639) was used to obtain the standard curve and the fluorescence change per unit sample of the experimental of the present invention.

TABLE 6

Fluorescent Values for Immobilized Papain
with 1% DMA and without DMA (Control)
Linked Papain samples with or without
1% DMA (12 week samples)

| | | | | | | | | |
|---|---|---|---|---|---|---|---|---|
| | | | | 4 C. | | | | |
| 1 | LP-1% DMA | 1:8 | 5674 | 5432 | 5876 | 5660.7 | 4415 | 0.458 |
| 2 | LP-Control | 1:8 | 4598 | 5165 | 5120 | 4961.0 | 3715 | 0.385 |
| | | | | 25 C. | | | | |
| 1 | LP-1% DMA | 1:8 | 5432 | 4987 | 4976 | 5131.7 | 3886 | 0.403 |
| 2 | LP-Control | 1:8 | 2204 | 2252 | 2359 | 2271.7 | 1026 | 0.103 |
| | | | | 40 C. | | | | |
| 1 | LP-1% DMA | 1:8 | 1903 | 1885 | 1849 | 1879.0 | 633 | 0.062 |
| 2 | LP-Control | 1:8 | 1580 | 1571 | 1575 | 1575.3 | 329 | 0.030 |
| | | | | 50 C. | | | | |
| 1 | LP-1% DMA | 1:8 | 1334 | 1345 | 1474 | 1384.3 | 138 | 0.010 |
| 2 | LP-Control | 1:8 | 1274 | 1315 | 1324 | 1304.3 | 58 | 0.001 |

TABLE 7

Activity of Immobilized Papain 1% with 1% DMA and immobilized
papain without DMA (Control) measured in units/ml.

| | | Activity units/ml | Units/ml | | | |
|---|---|---|---|---|---|---|
| 0 week | LP-1% DMA | 3.82 | 3.82 | 3.82 | 3.82 | |
| data Apr. 16, 2008 | LP-Control | 4.91 | 4.91 | 4.91 | 4.91 | |
| | | 4 C. | 25 C. | 40 C. | 50 C. | |
| 2 week | LP-1% DMA | 3.97 | 4.08 | 3.54 | 2.89 | |
| data Apr. 30, 2008 | LP-Control | 3.77 | 2.67 | 2.1 | 0.98 | |
| 4 week | LP-1% DMA | 3.89 | 3.75 | 2.65 | 1.02 | |
| data May 14, 2008 | LP-Control | 3.56 | 2.25 | 1.87 | 0.33 | |
| 6 week | LP-1% DMA | 3.74 | 3.66 | 2.11 | 0.5 | |
| data May 28, 2008 | LP-Control | 3.54 | 1.76 | 1.02 | 0.1 | |
| 8 week | LP-1% DMA | 3.67 | 3.54 | 1.41 | 0.09 | |
| data Jun. 11, 2008 | LP-Control | 3.33 | 1.09 | 0.5 | 0.01 | |
| 12 week | LP-1% DMA | 3.66 | 3.22 | 0.49 | 0.08 | |
| data Jul. 02, 2008 | LP-Control | 3.08 | 0.82 | 0.24 | 0.01 | |

In other experiments, crosslinked 1% papain was stored with 1% DMA and crosslinked 1% papain was stored without DMA at the temperatures of 4° C., 25° C. and 45° C. over a 12 week period to determine the stability of these papain samples at these temperatures. The results of this experiment was obtained by a papain activity assay using Invitrogen EnzChek® assay kit, N=3.

Figure 6A:
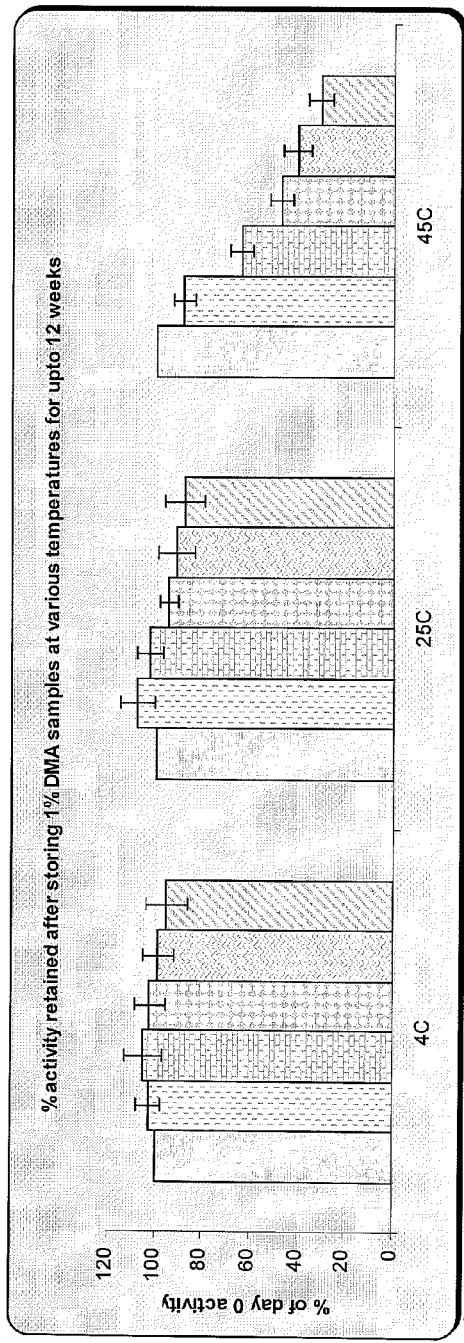
FIG. 6(a) illustrates the percentage of day 0 activity retained after storing stabilized papain samples at various temperatures for up to 12 weeks in accordance with an exemplary embodiment of the present invention.
Figure 6B:
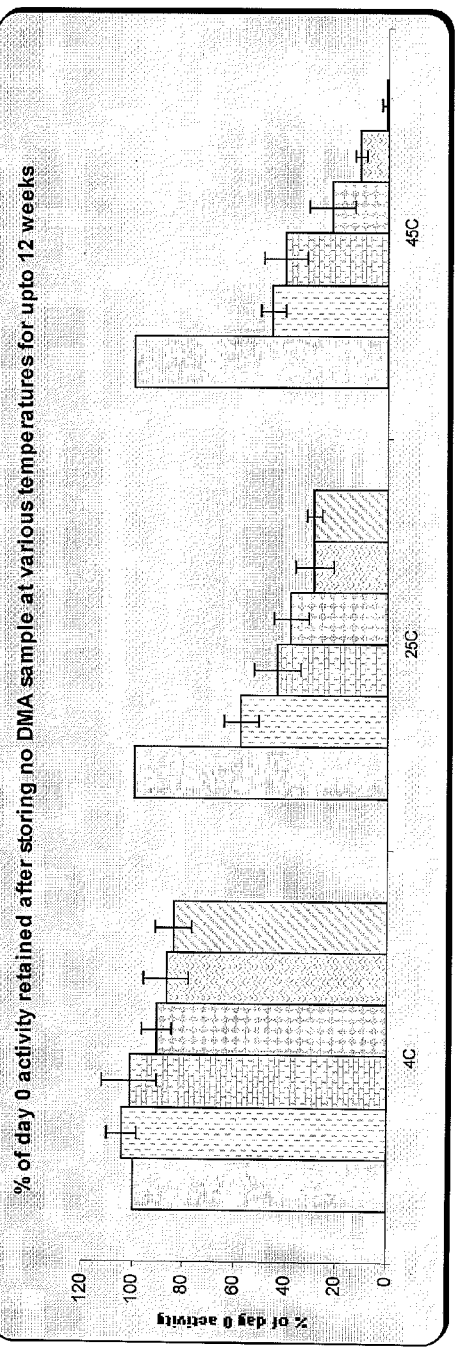
FIG. 6(b) illustrates the percentage of day 0 activity retained after storing the no DMA samples at various temperatures for up to 12 weeks.

As shown in FIGS. 6(a)-6(b), the crosslinking of immobilized papain with DMA significantly improved the stability of the product at 25° C. and 45° C. in comparison to the control sample in which linked papain was not stored with DMA. FIG. 6(a) illustrates the percentage of activity retained after storing samples for up to 12 weeks containing linked papain crosslinked by DMA. FIG. 6(b) illustrates control samples which are stored for up to 12 weeks containing linked papain with no DMA It is further noted that as illustrated in FIG. 6(a), it was determined that the linked papain product crosslinked by DMA retains over about 80% activity at 4° C. and 25° C. for 12 weeks and about 50% at 45° C.

Figure 7:
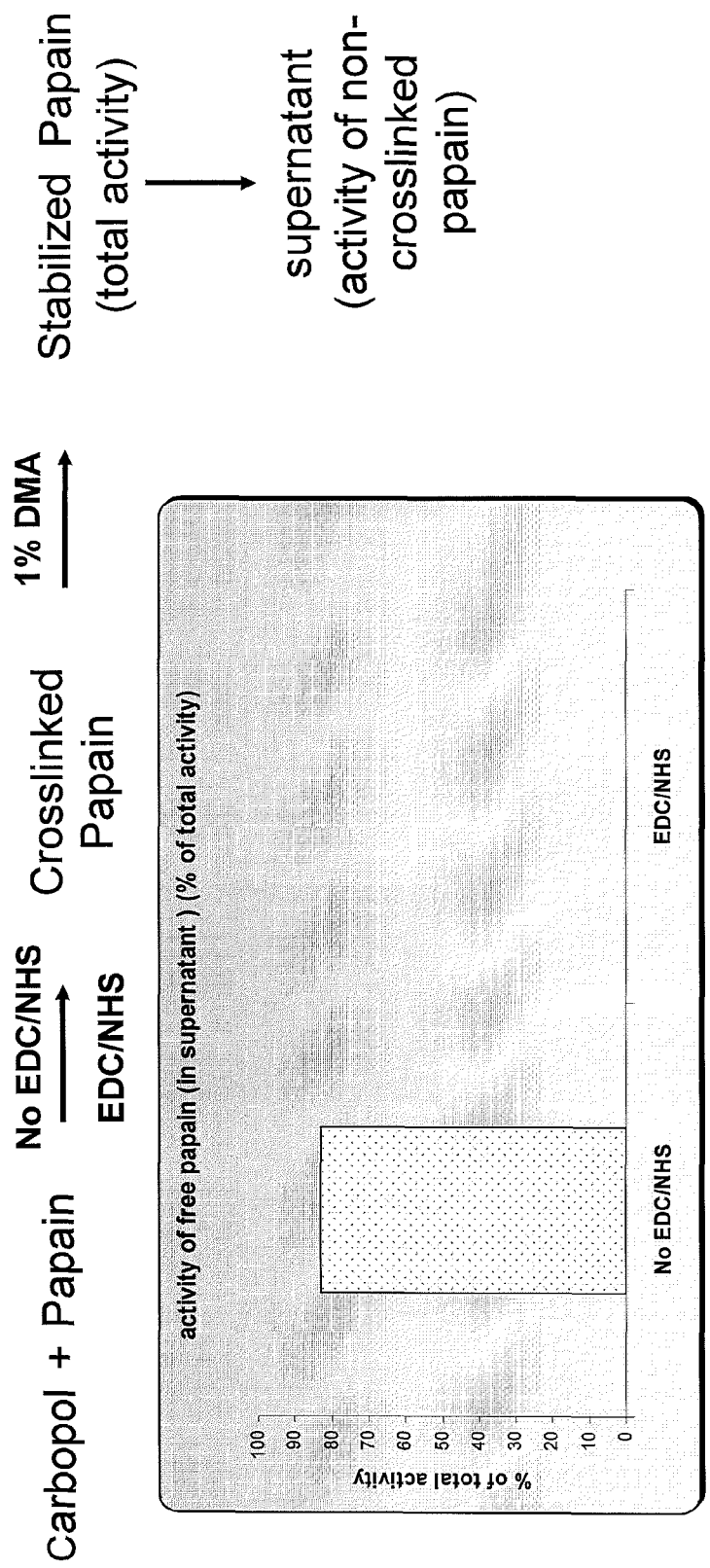
FIG. 7 is a chart which illustrates that no free active papin was found in a stable crosslinked papain product in accordance with an exemplary embodiment of the present invention.

In still other experiments, as shown in FIG. 7, a determination of free active papain in stabilized papain was conducted. The results of the experiment was that it was determined that there was no free active papain found in the papain that had been crosslinked by EDC/NHS in a primary cross-linking reaction and then further crosslinked by 1% DMA in a secondary crosslinking reaction in accordance with an exemplary embodiment of the present invention. On the other hand, there was significant activity of free papain in the papain of the control samples which was non-crosslinked.

Example 2

In example 2, instead of DMA being used as the secondary cross-linker, 0.2% of the crosslinker BS3 was used to crosslink the immobilized papain product in a secondary cross-linking reaction. The protocol, reactants, reaction conditions and results for determining the percentage of activity of the experimental samples of immobilized papain stored with 0.2% BS3 and control samples of immobilized papain stored without BS3 are illustrated in tables 8-10 and discussed below.

TABLE 8

Assay protocol using Invitrogen E6639 EnzChek kit for enzyme activity

Papain standard curve

| STD # | Stock Solution (U/ml) | Stock (1 U/ml) | Assay Buffer |
|---|---|---|---|
| 1 | 1 | 1000 | 0 |
| 2 | 0.5 | 500 | 500 |
| 3 | 0.25 | 250 | 750 |
| 4 | 0.1 | 100 | 900 |
| 5 | 0.05 | 50 | 950 |
| 6 | 0.01 | 10 | 990 |
| 7 | 0.005 | 5 | 995 |
| 8 | 0 | 0 | 1000 |

Prepare 1 Unit/ml stock solution of papain
10 mg Sigma papain
25 ml dl 1X digestion buffer
Material & buffer requirement:
0.1M Sodium Bicarbonate, pH 8.3
1x Digestion buffer: PBS pH 6 + 50 ul of TX-100
1 Mg/ml stock of BODIPY TRX casein = 1 vial of substrate and dissolve in 0.2 ml of Bicarbonate buffer
10 ug/ml working solution of BODIPY casein:
Add 0.2 mL of stock substrate in 19.8 ml of Digestion buffer in 50 ml falcon
Assay:   20 ul of STD/sample
        80 ul of 1X digestion buffer
        100 ul of 10 ug/mL working solution of BODIPY casein
Samples: 50 ul of linked papain mixed with 150 ul of 1X digestion buffer containing 0.1%
Triton X-100

TABLE 8-continued

Assay protocol using Invitrogen E6639 EnzChek kit for enzyme activity

Procedure:
Incubate the plate at room temperature for one hour with moderate agitation. Protect the plate from light. Read the fluorescence in a fluorescence microplate reader. Using standard fluorescence filters excitation 530/25 nm, emission 620/40 nm.

| Tube # | Sample ID Linked Papain Samples | Dilution Filter | Sample | 1X digestion buffer |
|---|---|---|---|---|
| 1 | LP-BS3 4 C. | 1:4 | 50 | 150 |
| 2 | LP-BS3 25 C. | 1:4 | 50 | 150 |
| 3 | LP-BS3 40 C. | 1:4 | 50 | 150 |
| 4 | LP-BS3 50 C. | 1:4 | 50 | 150 |
| 5 | LP-no BS3 4 C. | 1:4 | 50 | 150 |
| 6 | LP-no BS3 25 C. | 1:4 | 50 | 150 |
| 7 | LP-no BS3 40 C. | 1:4 | 50 | 150 |
| 8 | LP-no BS3 50 C. | 1:4 | 50 | 150 |
|   |   | 1:4 | 50 | 150 |

Linked papain samples were made with or without 0.2% BS3

TABLE 9

| Tube # | Sample ID | Dilution Factor | Read 1 | Read 2 | Read 3 | Average | average-negative | units/ml | units/ml |
|---|---|---|---|---|---|---|---|---|---|
| 1 | LP - BS3 4 C. | 1:4 | 10954 | 10883 | 12916 | 11584.3 | 10231 | 1.034 | 4.14 |
| 2 | LP - BS3 25 C. | 1:4 | 12196 | 12865 | 12959 | 12673.3 | 11320 | 1.156 | 4.62 |
| 3 | LP - BS3 40 C. | 1:4 | 13135 | 13636 | 14267 | 13679.3 | 12326 | 1.268 | 5.07 |
| 4 | LP - BS3 50 C. | 1:4 | 11009 | 11025 | 11031 | 11021.7 | 9668 | 0.971 | 3.89 |
| 5 | LP - no BS3 4 C. | 1:4 | 8174 | 19586 | 12 | 9257.3 | 7904 | 0.775 | 3.10 |
| 6 | LP - no BS3 25 C. | 1:4 | 5345 | 12494 | 13 | 5950.7 | 4597 | 0.406 | 1.62 |
| 7 | LP - no BS3 40 C. | 1:4 | 3191 | 7654 | 12 | 3619.0 | 2265 | 0.146 | 0.58 |
| 8 | LP - no BS3 50 C. | 1:4 | 2383 | 5583 | 14 | 2660.0 | 1306 | 0.039 | 0.16 |

TABLE 10

| Activity retained after 1 week - % of 4 C. activity | No BS3 | 0.2% BS3 |
|---|---|---|
| 4 C. | 99.957 | 99.912 |
| 25 C. | 52.389 | 111.643 |
| 40 C. | 18.847 | 122.479 |
| 50 C. | 5.052 | 93.851 |

Figure 8:
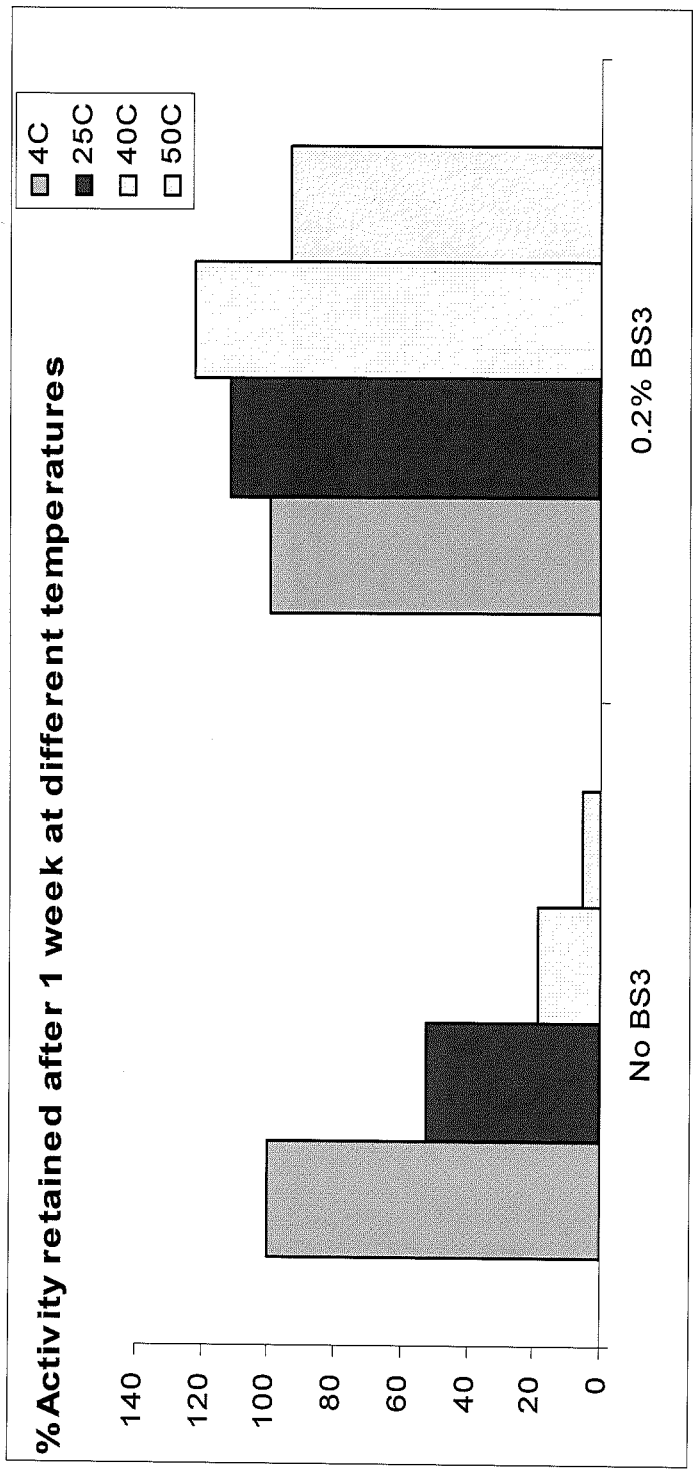
FIG. 8 is a chart which illustrates the percentage of activity after 1 week at different temperatures of samples which contain 0.2% of BS3 and control samples which do not contain any BS3.

As can be seen from the results of table 10 and FIG. 8, the activity of immobilized 1% papain which has been further crosslinked with 0.2% BS3 was significantly greater over a variety of temperatures than the activity of immobilized papain in the control samples which was not reacted with BS3.

Example 3

In this example, 1% stabilized papain and 0.1% sodium alginate were combined. The protocol, reactants, reaction conditions and results for determining the % of activity of experimental samples of stabilized papain stored with 0.1% sodium alginate and control samples of stabilized papain product stored without sodium alginate are discussed below.

TABLE 11

Papain standard curve

Prepare 5 Unit/mL stock solution of papain
10 mg Sigma papain
5 ml dl 1X digestion buffer
Material & buffer requirement:
1X assay buffer: 50 mM borate pH 8.5
Substrate: 2 mg/ml succinylated casein in 1X assay buffer, dissolve 1 vial (10 mg) in 5 ml assay buffer TNBSA working soln: 100 ul of TNBSA stock to 14.9 ml of assay buffer
Assay: 50 ul of STD/sample
100 ul of substrate (2 mg/ml), incubate the plate for 20 min at RT
50 ul of TNBSA solution, incubate the plate for 20 mins at room temp
Read absorbance at 450 nm
Samples tested (4 week linked papain samples - prepared on 101607 papain concentration 1%)
No treatment 4 C.
0.1% Alginate 4 C.
No treatment 25 C.
0.1% Alginate 25 C.

TABLE 11-continued

No treatment 50 C.
0.1% Alginate 50 C.

TABLE 12

| standard papain | value 1 | value 2 | average | negative | ave-neg absorbance 450 nm |
|---|---|---|---|---|---|
| 3 | 1.636 | 1.677 | 1.6565 | 0.676 | 0.9805 |
| 2 | 1.161 | 1.16 | 1.1605 | 0.427 | 0.7335 |
| 1 | 0.554 | 0.55 | 0.552 | 0.232 | 0.32 |
| 0.5 | 0.245 | 0.245 | 0.245 | 0.12 | 0.125 |
| 0.25 | 0.123 | 0.127 | 0.125 | 0.071 | 0.054 |
| 0.1 | 0.073 | 0.075 | 0.074 | 0.049 | 0.025 |
| 0.05 | 0.06 | 0.06 | 0.06 | 0.042 | 0.018 |
| 0 | 0.054 | 0.061 | 0.0575 | 0.031 | 0.0265 |

TABLE 13 samples tested (4 week linked papain samples - prepared on Oct. 16, 2007 papain concentration 1%))

|   | value 1 | value 2 | average | negative | ave-neg | units/ml |
|---|---|---|---|---|---|---|
| No treatment 4 C. | 1.455 | 1.15 | 1.3025 | 0.7145 | 0.588 | 1.754939546 |
| 0.1% Alginate 4 C. | 1.328 | 1.329 | 1.3285 | 0.6123 | 0.7162 | 2.132999115 |

TABLE 13-continued samples tested (4 week linked papain samples - prepared on Oct. 16, 2007 papain concentration 1%))

| | | | | | | |
|---|---|---|---|---|---|---|
| No treatment 25 C. | 0.758 | 0.629 | 0.6935 | 0.5605 | 0.133 | 0.413152462 |
| 0.1% Alginate 25 C. | 0.936 | 0.9 | 0.918 | 0.563 | 0.355 | 1.0678266 |
| No treatment 50 C. | 0.691 | 0.778 | 0.7345 | 0.734 | 0.0005 | 0.022412268 |
| 0.1% Alginate 50 C. | 0.791 | 0.746 | 0.7685 | 0.6776 | 0.0909 | 0.289000295 | week 1

| | week 0 units/ml | units/ml | | | % of week o activity | | |
|---|---|---|---|---|---|---|---|
| | | week 1- 4 C. | week 1- 25 C. | week 1 - 50 C. | week 1- 4 C. | week 1- 25 C. | week 1 - 50 C. |
| No treatment | 2.690 | 2.292 | 0.777 | 0.143 | 85.22 | 28.9 | 5.31 |
| alginate | 2.795 | 2.581 | 1.546 | 0.986 | 92.36 | 55.32 | 35.26 | week 2

| | week 0 units/ml | units/ml | | | % of week o activity | | |
|---|---|---|---|---|---|---|---|
| | | week 2- 4 C. | week 2- 25 C. | week 2 - 50 C. | week 2- 4 C. | week 2- 25 C. | week 2 - 50 C. |
| No treatment | 2.690 | 2.113 | 0.673 | 0.032 | 78.56 | 25 | 1.2 |
| alginate | 2.795 | 2.550 | 1.258 | 0.894 | 91.23 | 45 | 32 | week 3

| | week 0 units/ml | units/ml | | | % of week o activity | | |
|---|---|---|---|---|---|---|---|
| | | week 3- 4 C. | week 3- 25 C. | week 3 - 50 C. | week 3- 4 C. | week 3- 25 C. | week 3 - 50 C. |
| No treatment | 2.6902 | 1.89 | 0.60 | 0.03 | 70.24 | 22.32 | 1.03 |
| alginate | 2.7950 | 2.24 | 1.13 | 0.59 | 80.23 | 40.32 | 21.01 | week 4

| | week 0 units/ml | units/ml | | | % of week o activity | | |
|---|---|---|---|---|---|---|---|
| | | week 4- 4 C. | week 4- 25 C. | week 4 - 50 C. | week 4- 4 C. | week 4- 25 C. | week 4 - 50 C. |
| No treatment | 2.690 | 1.7549 | 0.4132 | 0.0224 | 65.2394 | 15.3588 | 0.8332 |
| alginate | 2.795 | 2.1330 | 1.0678 | 0.2890 | 76.3148 | 38.2049 | 10.3399 |

| | % of week 0 activity | | |
|---|---|---|---|
| | week 4- 4 C. | week 4- 25 C. | week 4 - 50 C. |
| No treatment | 65.239 | 15.359 | 0.833 |
| 0.1% Alginate | 76.315 | 38.205 | 10.340 |

Figure 9:
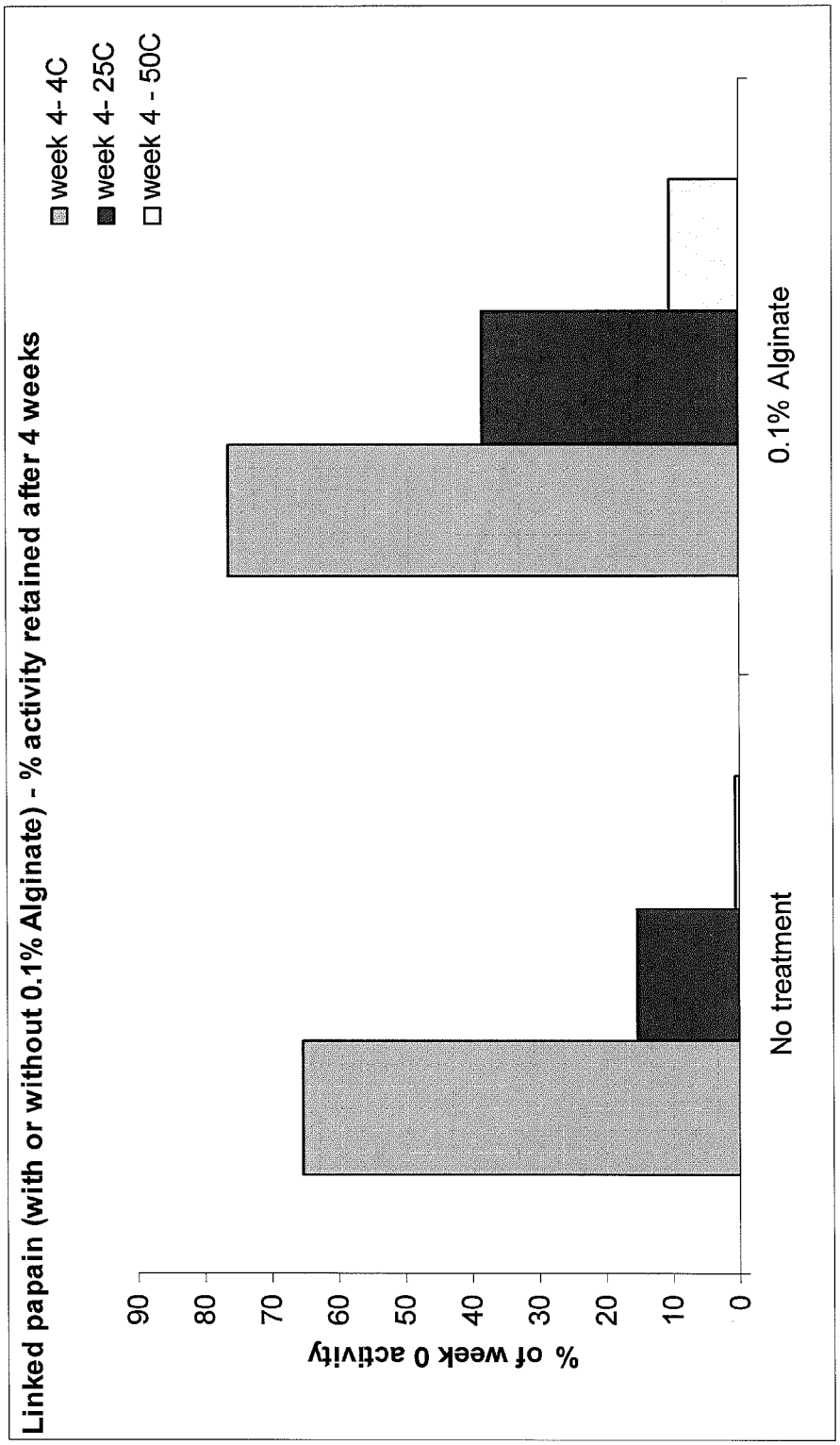
FIG. 9 is a chart which illustrates the percentage of retained activity after 4 weeks of samples of stabilized papain with and without 0.1% alginate.

As can be seen from the results of table 13, the activity of stabilized papain which was stored with 0.1% sodium alginate is significantly greater over a variety of temperatures over 4 weeks than the activity of stabilized papain in the control samples which was not stored with sodium alginate. Accordingly, linked papain reacted with 0.1% sodium alginate is significantly more stable than the control samples of papain mentioned above which do not include sodium alginate. Furthermore, FIG. 9 illustrates the results of table 13 that the activity of stabilized papain with sodium alginate was significantly greater over a variety of temperatures over 4 weeks than the activity of crosslinked papain in the control samples which did not include sodium alginate.

Figure 10:
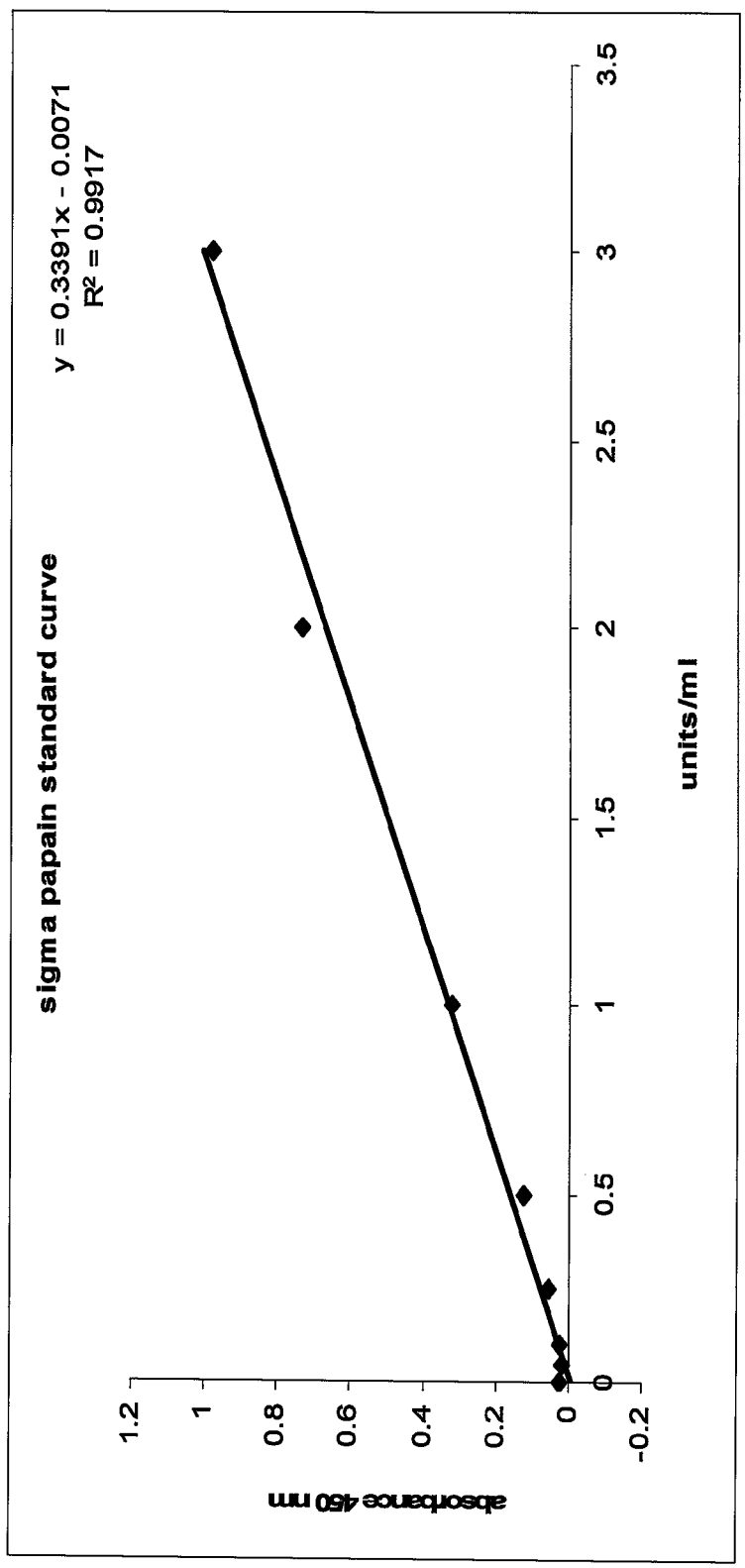
FIG. 10 is a sigma papain standard curve.

Furthermore, as shown in FIG. 10, a Sigma papain activity standard curve using absorbance vs. units/ml was developed for assisting in quantitating the activity of linked 1% papain together with 0.1% sodium alginate.

Figure 11:
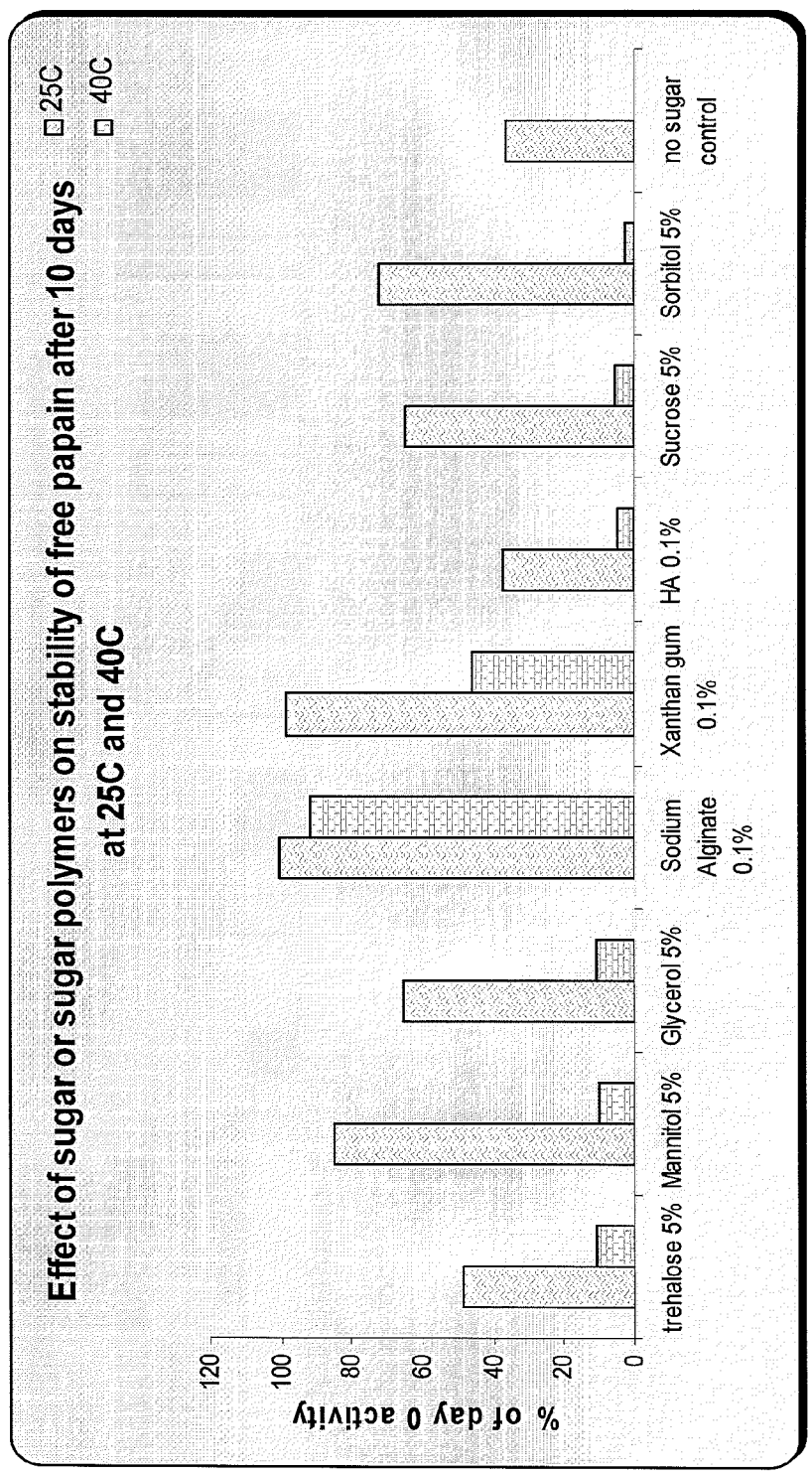
FIG. 11 is a chart which illustrates the effect of sugar or sugar polymers on the stability of free papain after 10 days at 25° C. and 40° C.

In other experiments, as shown in FIG. 11, the effect of sugar and sugar polymers on the stability of free papain after days at 25° C. and 40° C. were conducted. The sugar or sugar polymers included were 0.1% sodium alginate, 5% trehalose, 5% Mannitol, 5% Glycerol, 0.1 xanthan gum, 0.1% HA, 5% sucrose, 5% sorbitol and a no sugar control. From the results it is noted that 0.1% sodium alginate was found to have a stabilizing effect on free papain. This stabilizing effect of 0.1% sodium alginate was also observed on the stabilized papain of the present invention as well.

Figure 12:
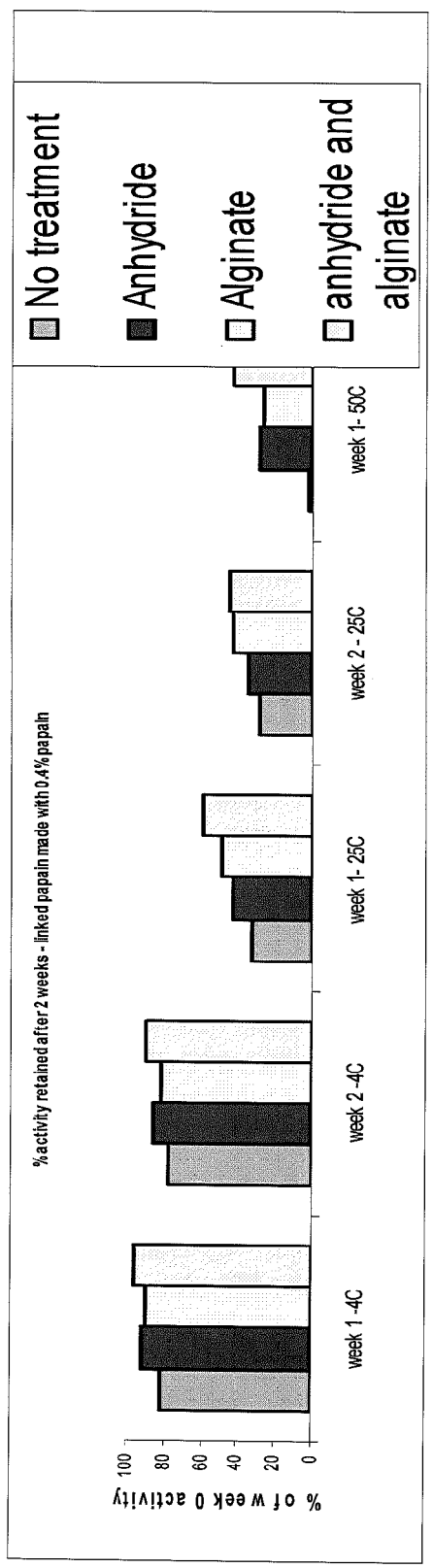
FIG. 12 is a chart which illustrates the percentage of activity retained after 2 weeks of 0.4% papain.

In still other experiments, as shown in FIG. 12, the percentage of the activity retained after 2 weeks of stabilized papain made with 0.4% papain was determined. In some samples of these experiments, the linked papain was treated with sodium alginate, in some samples the linked papain was treated with anhydride, in some samples the linked papain was treated with anhydride and sodium alginate and in some samples the linked papain was not treated at all with any of the above. As can be gleaned from FIG. 12, the samples which were treated with both sodium alginate and anhydride had the greatest % activity retained after each of the two weeks and the samples which were not treated at all had the lowest % activity retained after each of the two weeks.

Example 4

In example 4, immobilized papain was reacted with 1% DMA for secondary crosslinking and with 0.1% sodium alginate for further stability and included as part of a preservative system which comprises 1.2% phenoxyethanol+0.2% benzoic acid. The protocol, reactants, reaction conditions and results for determining the % of activity of experimental samples of stabilized papain in accordance with one embodiment of the present invention and control samples of a linked papain product (without DMA or sodium alginate) shown in Table 14 and are discussed below.

TABLE 14

Assay protocol using Invitrogen E6639 EnzChek kit for enzyme activity

Papain standard curve

| STD # | Stock solution (U/mL) | Stock (1 U/mL) | Assay buffer |
|---|---|---|---|
| 1 | 1 | 1000 | 0 |
| 2 | 0.5 | 500 | 500 |
| 3 | 0.25 | 250 | 750 |
| 4 | 0.1 | 100 | 900 |
| 5 | 0.05 | 50 | 950 |
| 6 | 0.01 | 10 | 990 |
| 7 | 0.005 | 5 | 995 |
| 8 | 0 | 0 | 1000 |

Prepare 1 Unit/mL stock solution of papain
10 mg Sigma papain
25 ml dl 1X digestion buffer
Material & buffer requirement:
0.1M Sodium Bicarbonate, pH 8.3
1x Digestion buffer: PBS pH 6 + 50 ul of TX-100
1 Mg/ml stock of BODIPY TRX casein = 1 vial of substrate and dissolve in 0.2 ml of Bicarbonate buffer
10 ug/mL working solution of BODIPY casein:
Add 0.2 mL of stock substrate in 19.8 ml of Digestion buffer in 50 ml falcon
Assay: 20 ul of STD/sample
80 ul of 1X digestion biffer
100 ul of 10 ug/mL working solution of BODIPY casein

| Samples tested contain | 1% DMA samples | control |
|---|---|---|
| | 1% papain 600 (ESP) | 1% papain 600 (ESP) |
| | 1% DMA | no DMA |
| | 0.1% Alginate | 0.1% Alginate |
| | 1.2% phenoxyethanol | 1.2% phenoxyethanol |
| | 0.2% Benzoic acid | 0.2% Benzoic acid |
| Samples: | 25 ul of linked papain mixed with 150 ul of 1X digestion buffer containing 0.1% Triton X-100 | |

Procedure:
Incubate the plate at room temperature for one hour with moderate agitation. Protect the plate from light. Read the flurescence in a fluorescence microplate reader. Using standard fluorescein filters excitation 590/25 nm, emission 620/40 nm.

TABLE 15

Linked papain samples with varying conc of other crosslinker (12 week samples)

4 C.

| | | | | |
|---|---|---|---|---|
| 1 | LP - 1% DMA | 1:8 | 25 | 175 |
| 2 | LP-control | 1:8 | 25 | 175 |

25 C.

| 1 | LP - 1% DMA | 1:8 | 25 | 175 |
|---|---|---|---|---|
| 2 | LP-control | 1:8 | 25 | 175 |

45 C.

| 1 | LP - 1% DMA | 1:8 | 25 | 175 |
|---|---|---|---|---|
| 2 | LP-control | 1:8 | 25 | 175 |

Linked papain samples with or without 1% DMA (12 week samples)

4 C.

| 1 | LP - 1% DMA | 1:8 | 5321 | 5467 | 5562 | 5450.0 | 4223 | 0.580 | 4.64 |
|---|---|---|---|---|---|---|---|---|---|
| 2 | LP-control | 1:8 | 4578 | 4879 | 5098 | 4851.7 | 3625 | 0.485 | 3.88 |

25 C.

| 1 | LP - 1% DMA | 1:8 | 5098 | 5291 | 5120 | 5169.7 | 3943 | 0.535 | 4.28 |
|---|---|---|---|---|---|---|---|---|---|
| 2 | LP-control | 1:8 | 2789 | 2908 | 2871 | 2856.0 | 1629 | 0.169 | 1.35 |

45 C.

| 1 | LP - 1% DMA | 1:8 | 2987 | 2871 | 3091 | 2983.0 | 1756 | 0.189 | 1.51 |
|---|---|---|---|---|---|---|---|---|---|
| 2 | LP-control | 1:8 | 1765 | 1775 | 1879 | 1806.3 | 579 | 0.002 | 0.02 |

| 12 week data | 4 C. | 25 C. | 45 C. |
|---|---|---|---|
| LP - 1% DMA | 4.638 | 4.283 | 1.511 |
| LP-control | 3.880 | 1.350 | 0.019 |

| | | 4 C. | 25 C. | 45 C. |
|---|---|---|---|---|
| | | | units/ml | | activity units/ml

| | | | 4 C. | 25 C. | 45 C. |
|---|---|---|---|---|---|
| 0 week data | | LP - 1% DMA | 4.87 | 4.87 | 4.87 |
| | | LP-control | 4.61 | 4.61 | 4.61 |
| 2 week data | | LP - 1% DMA | 5.01 | 5.25 | 4.31 |
| | | LP-control | 4.81 | 2.67 | 2.1 |
| 4 week | | LP - 1% DMA | 5.12 | 4.98 | 3.11 |

TABLE 15-continued

|  | | | | |
|---|---|---|---|---|
| data | LP-control | 4.67 | 2.01 | 1.87 |
| 6 week | LP - 1% DMA | 4.98 | 4.61 | 2.31 |
| data | LP-control | 4.18 | 1.76 | 1.02 |
| 8 week | LP - 1% DMA | 4.81 | 4.44 | 1.98 |
| data | LP-control | 4.01 | 1.35 | 0.5 |
| 12 week | LP - 1% DMA | 4.64 | 4.28 | 1.51 |
| data | LP-control | 3.88 | 1.35 | 0.02 |
| % activity retained after storing | | | | |
| 2 week | LP - 1% DMA | 102.87 | 107.80 | 88.50 |
| data | LP-control | 104.34 | 57.92 | 45.55 |
| 4 week | LP - 1% DMA | 105.13 | 102.26 | 63.86 |
| data | LP-control | 101.30 | 43.60 | 40.56 |
| 6 week | LP - 1% DMA | 102.26 | 94.66 | 47.43 |
| data | LP-control | 90.67 | 38.18 | 22.13 |
| 8 week | LP - 1% DMA | 98.77 | 91.17 | 40.66 |
| data | LP-control | 86.98 | 29.28 | 10.85 |
| 12 week | LP- 1% DMA | 95.24 | 87.94 | 31.02 |
| data | LP-control | 84.16 | 29.28 | 0.43 |

Figure 13A:
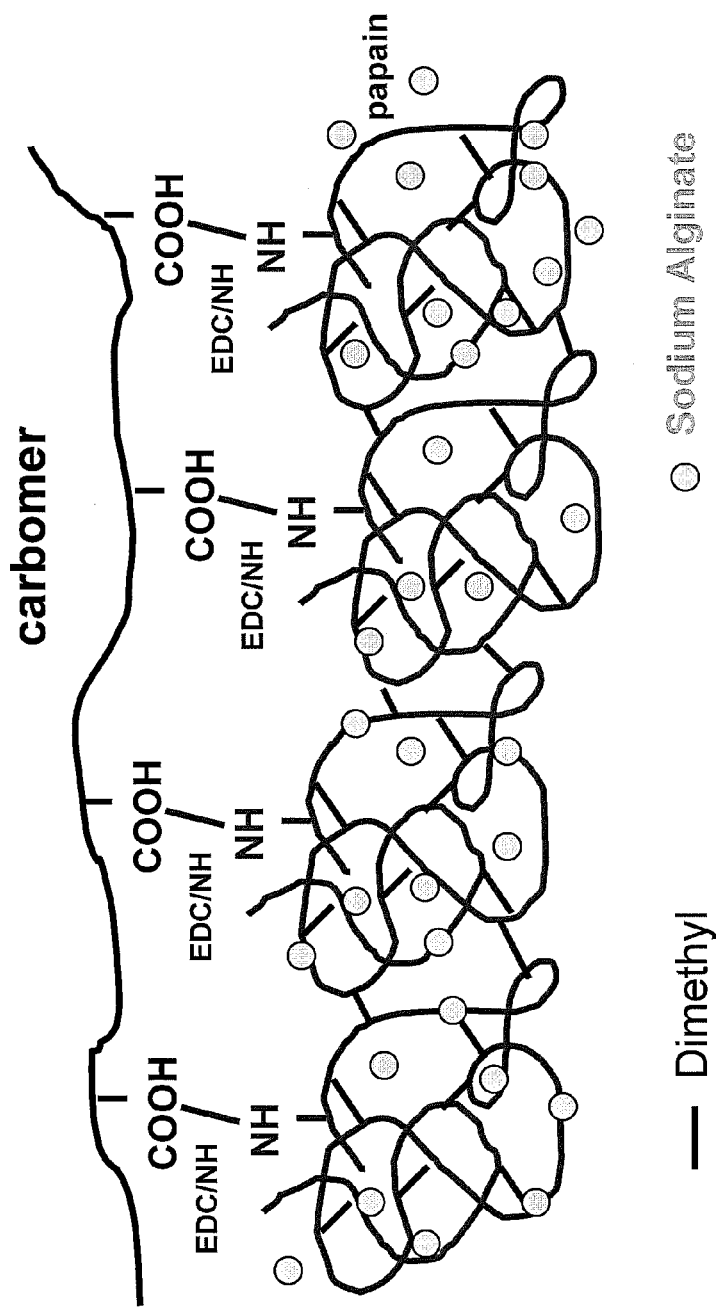
FIG. 13(a) illustrates a stable crosslinked papain product which has been crosslinked by DMA and has been further reacted with sodium alginate.

As noted above, the experimental samples in accordance with an exemplary embodiment of the present invention includes 1% DMA, 1% papain 600 (ESP), 0.1% sodium alginate, 1.2 phenoxyethanol+0.2% benzoic acid. The control samples included all the same components as the experimental formulation sample, except the control samples did not include DMA. The results for effect of DMA on the retention activity of linked papain over a 12 week period at various temperatures are set forth below. Moreover, the chemistry of the DMA, linked papain and the sodium alginate are illustrated in FIG. 13(a)

Figure 13B:
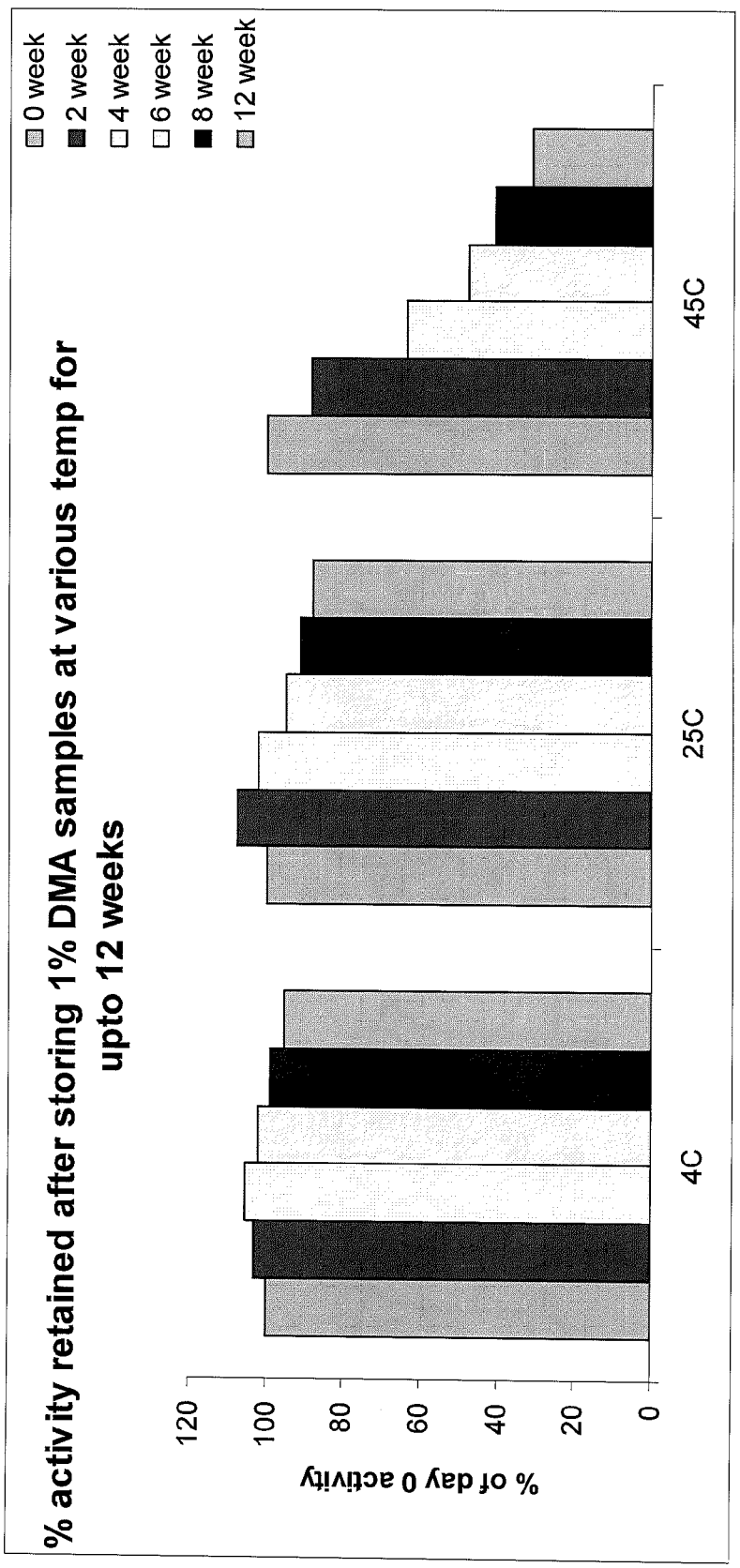
FIG. 13(b) is a chart which illustrates the percentage of activity retained after storing 1% DMA samples at various temperatures for up to 12 weeks.
Figure 13C:
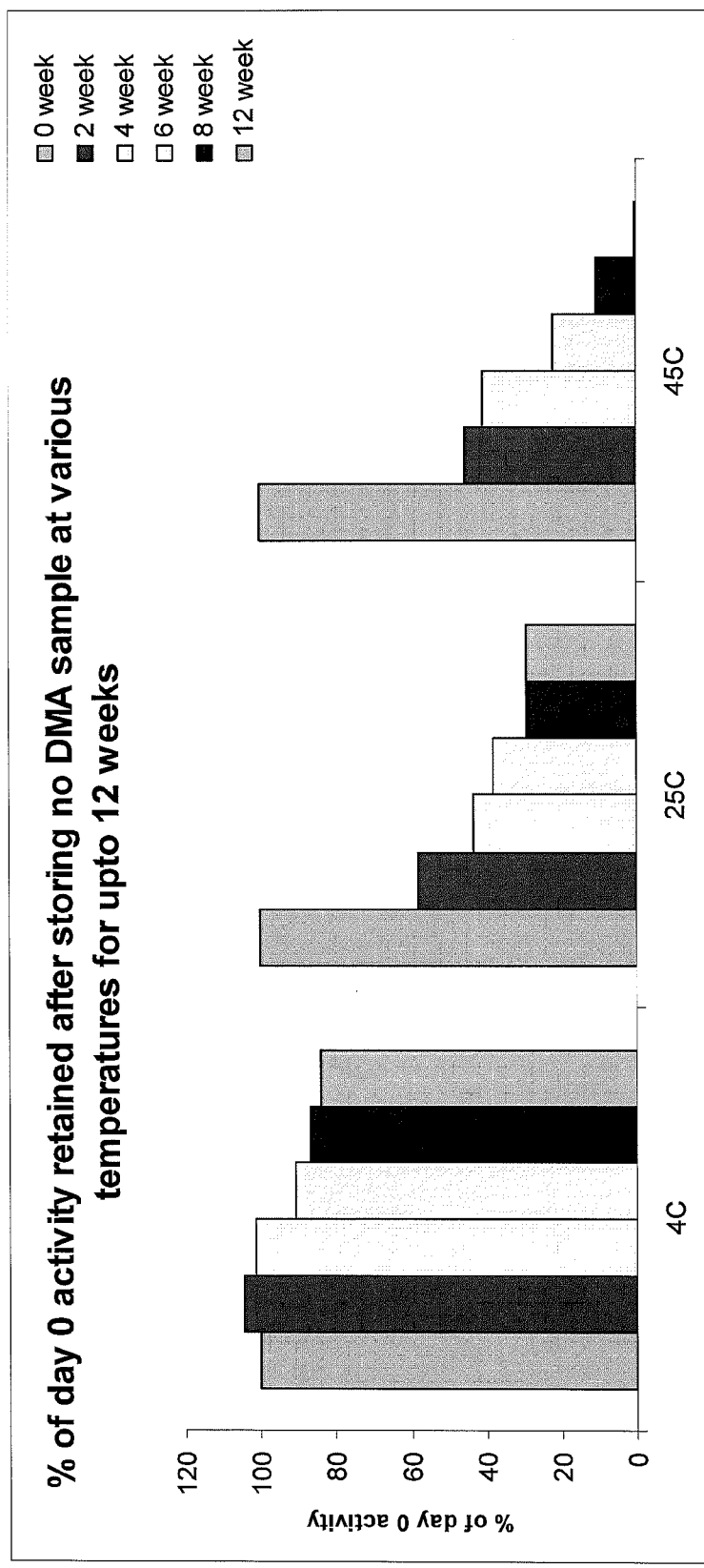
FIG. 13 (c) a chart which illustrates the percentage of day 0 activity after storing no DMA samples at various temperatures for up to 12 weeks.
Figure 14:
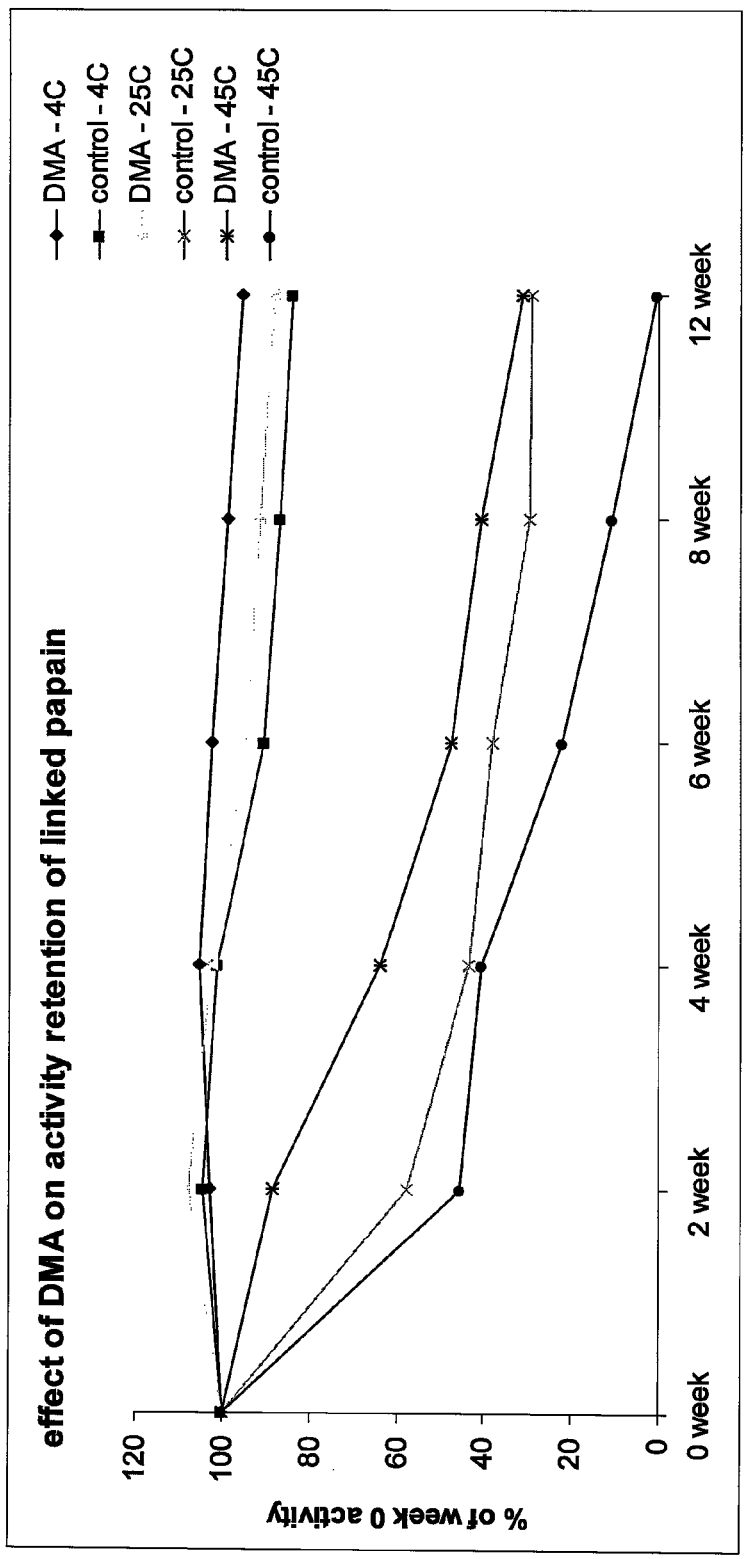
FIG. 14 is a graph which illustrates the effect of DMA on activity retention of linked papain.
Figure 15:
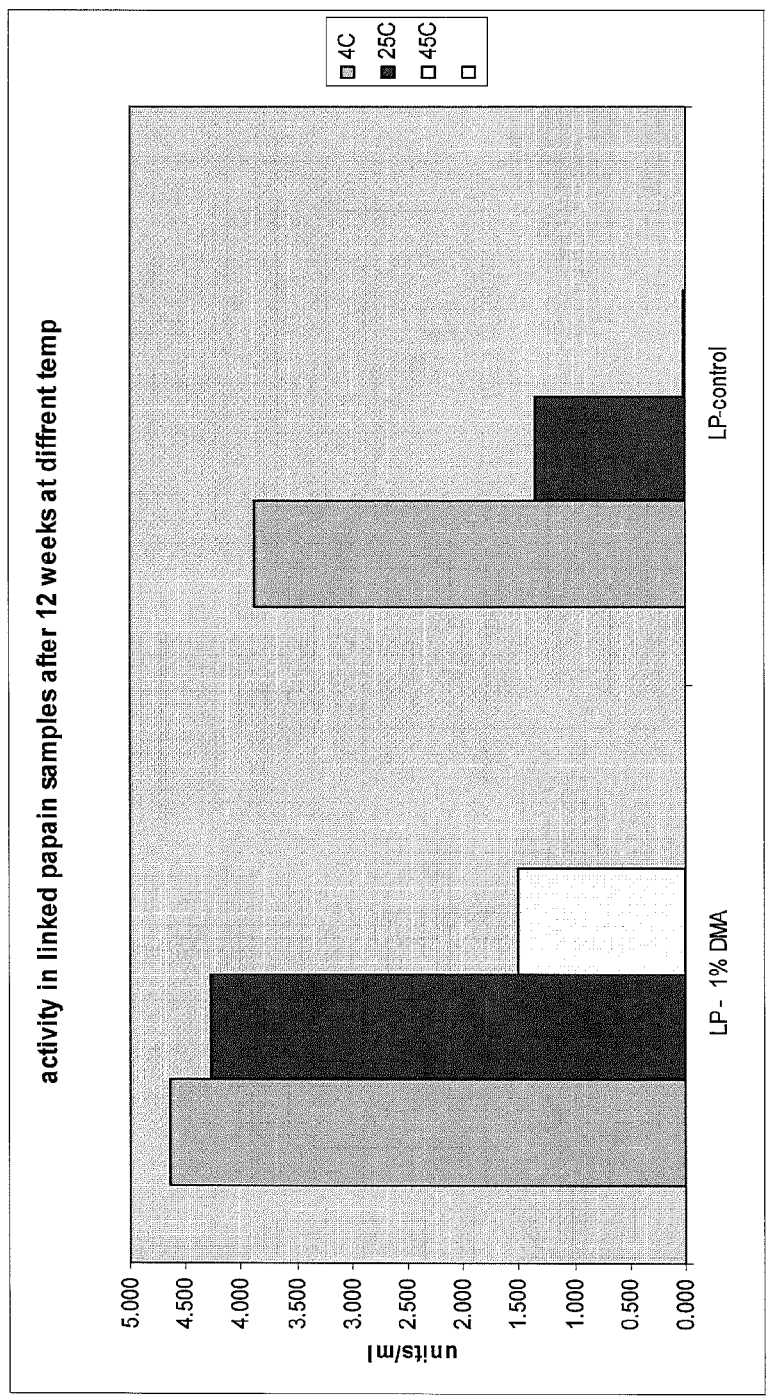
FIG. 15 is a chart which illustrates the activity in linked papain samples after 12 weeks at different temperatures.

As can be gleaned from the above data and FIGS. 13 (b), 13(c), 14 and 15, the crosslinking of linked papain with 1% DMA significantly improved the stability of the linked papain product over a variety of temperatures over a 12 week period in comparison to the control samples which did not contain any DMA.

Figure 16:
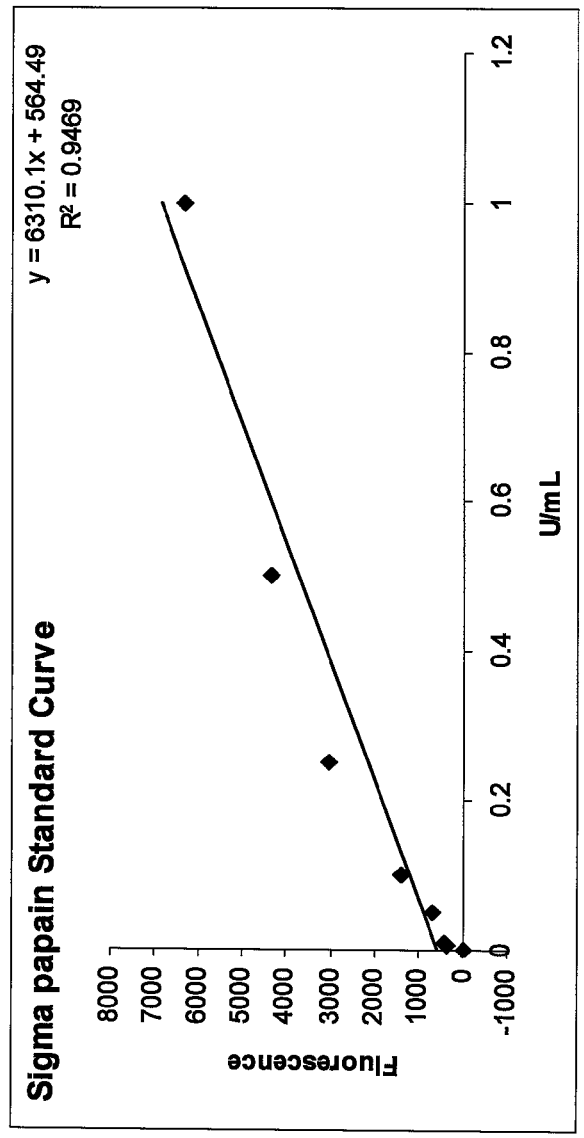
FIG. 16 is a Sigma papain standard curve.

Furthermore, as set forth above in table 15, papain activity in the experimental sample and the control were determined based upon fluorescence change per unit sample of the linked papain. A Sigma papain standard curve as shown in FIG. 16 was developed for assistance in quantitating the activity of immobilized 1% papain which was further crosslinked with 1% DMA in accordance with the present embodiment. As noted above, an EnzChek® protease assay kit (E-6639) was used to obtain the standard curve and the fluorescence change per unit sample of the experimental samples of immobilized papain with DMA in accordance with the present exemplary embodiment and the control samples without DMA.

Example 5

In another exemplary embodiment, immobilized papain was reacted with 5% DMA for further crosslinking and with 0.1% sodium alginate and included as part of the preservative system which comprises 1.2% phenoxyethanol+0.2% benzoic acid. The protocol and results for this embodiment are set forth below. The placebo formulation contains all of the components of the experimental formulation, except for DMA.

TABLE 16

| 11 week Formulation samples | Dilution Factor | Read 1 | Read 2 | Read 3 | Average | average-negative | units/ml | units/ml |
|---|---|---|---|---|---|---|---|---|
| 4 C. | | | | | | | | |
| 963030/1 | 1:4 | 1245 | 1342 | 1290 | 1292.3 | 151 | 0.055 | 0.22 |
| 963030/3 | 1:4 | 1677 | 1549 | 1682 | 1636.0 | 495 | 0.244 | 0.97 |
| 25 C. | | | | | | | | |
| 963030/1 | 1:4 | 1245 | 1232 | 1310 | 1262.3 | 121 | 0.039 | 0.15 |
| 963030/3 | 1:4 | 1581 | 1621 | 1590 | 1597.3 | 456 | 0.222 | 0.89 |
| 45 C. | | | | | | | | |
| 963030/1 | 1:4 | 1245 | 1154 | 1167 | 1188.7 | 48 | −0.002 | −0.01 |
| 963030/3 | 1:4 | 1576 | 1582 | 1501 | 1553.0 | 412 | 0.198 | 0.79 |

| 11 week formulation samples | | | 4 C. | | 25 C. | | 45 C. | |
|---|---|---|---|---|---|---|---|---|
| 963030/1 | | | 0.22 | | 0.15 | | −0.01 | |
| 963030/3 | | | 0.97 | | 0.89 | | 0.79 | |

| | | formula number | 4 C. | 25 C. | 45 C. |
|---|---|---|---|---|---|
| 0 week samples | placebo | 963030/1 | 0.98 | 0.98 | 0.98 |
| | 5% DMA sample | 963030/3 | 1.09 | 1.09 | 1.09 |

TABLE 16-continued

| | | | | | |
|---|---|---|---|---|---|
| 2 week samples | placebo | 963030/1 | 0.85 | 0.82 | 0.41 |
| | 5% DMA sample | 963030/3 | 1.12 | 1.21 | 1.05 |
| 4 week samples | placebo | 963030/1 | 0.61 | 0.71 | 0.31 |
| | 5% DMA sample | 963030/3 | 1.02 | 1.02 | 0.92 |
| 8 week samples | placebo | 963030/1 | 0.44 | 0.31 | 0.15 |
| | 5% DMA sample | 963030/3 | 1.00 | 0.95 | 0.85 |
| 11 week samples | placebo | 963030/1 | 0.22 | 0.15 | −0.01 |
| | 5% DMA sample | 963030/3 | 0.97 | 0.89 | 0.79 |
| % Of week 0 activity | | | | | |
| 2 week samples | placebo | 963030/1 | 86.73 | 83.67 | 41.84 |
| | 5% DMA sample | 963030/3 | 102.75 | 111.01 | 96.33 |
| 4 week samples | placebo | 963030/1 | 62.24 | 72.45 | 31.63 |
| | 5% DMA sample | 963030/3 | 93.58 | 93.58 | 84.40 |
| 8 week samples | placebo | 963030/1 | 44.90 | 31.63 | 15.31 |
| | 5% DMA sample | 963030/3 | 91.74 | 87.16 | 77.98 |
| 11 week samples | placebo | 963030/1 | 22.47 | 15.75 | −0.74 |
| | 5% DMA sample | 963030/3 | 89.38 | 81.60 | 72.67 |

Figure 17:
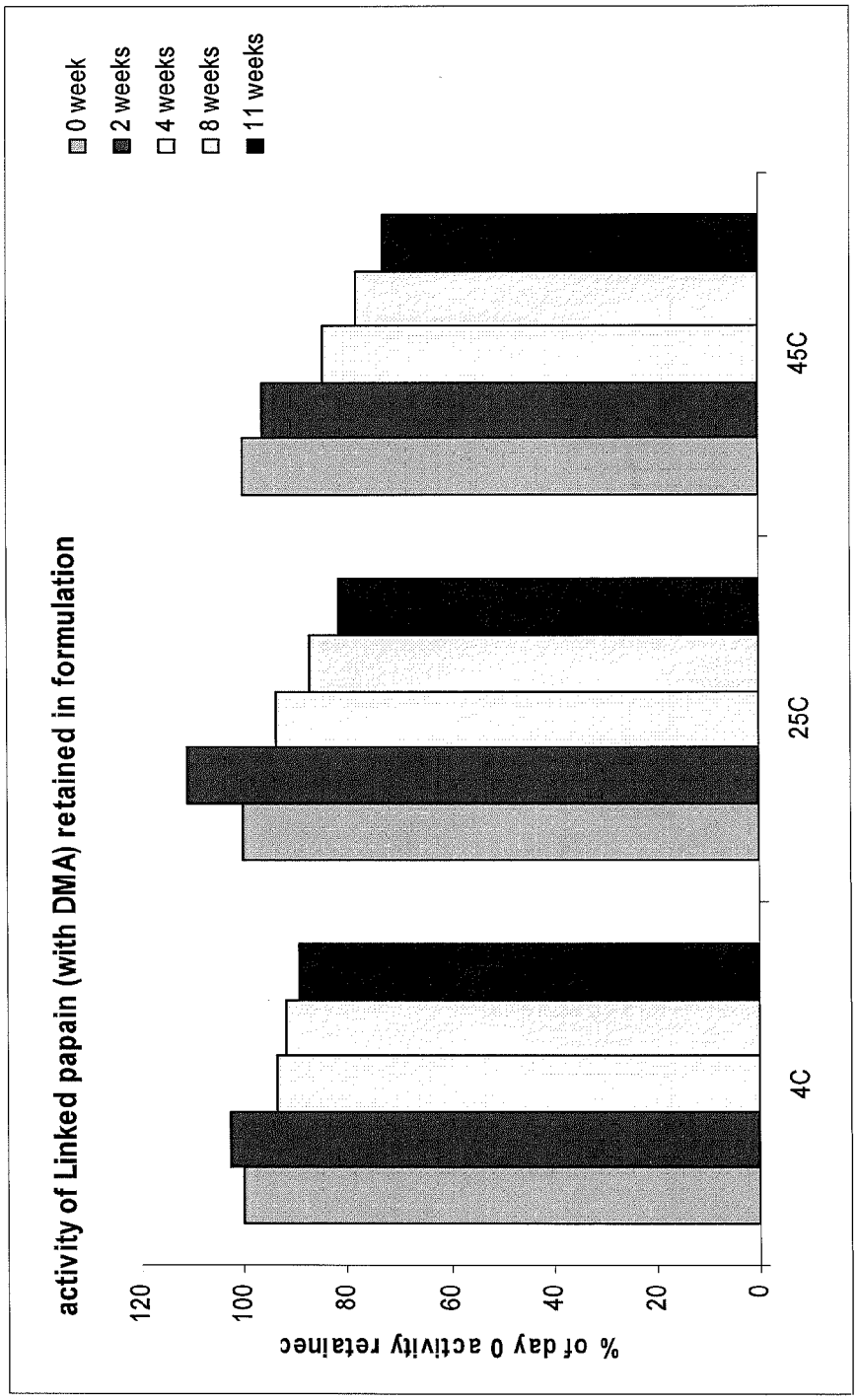
FIG. 17 is a chart which illustrates activity of linked papain (with DMA) retained in formulation.
Figure 18:
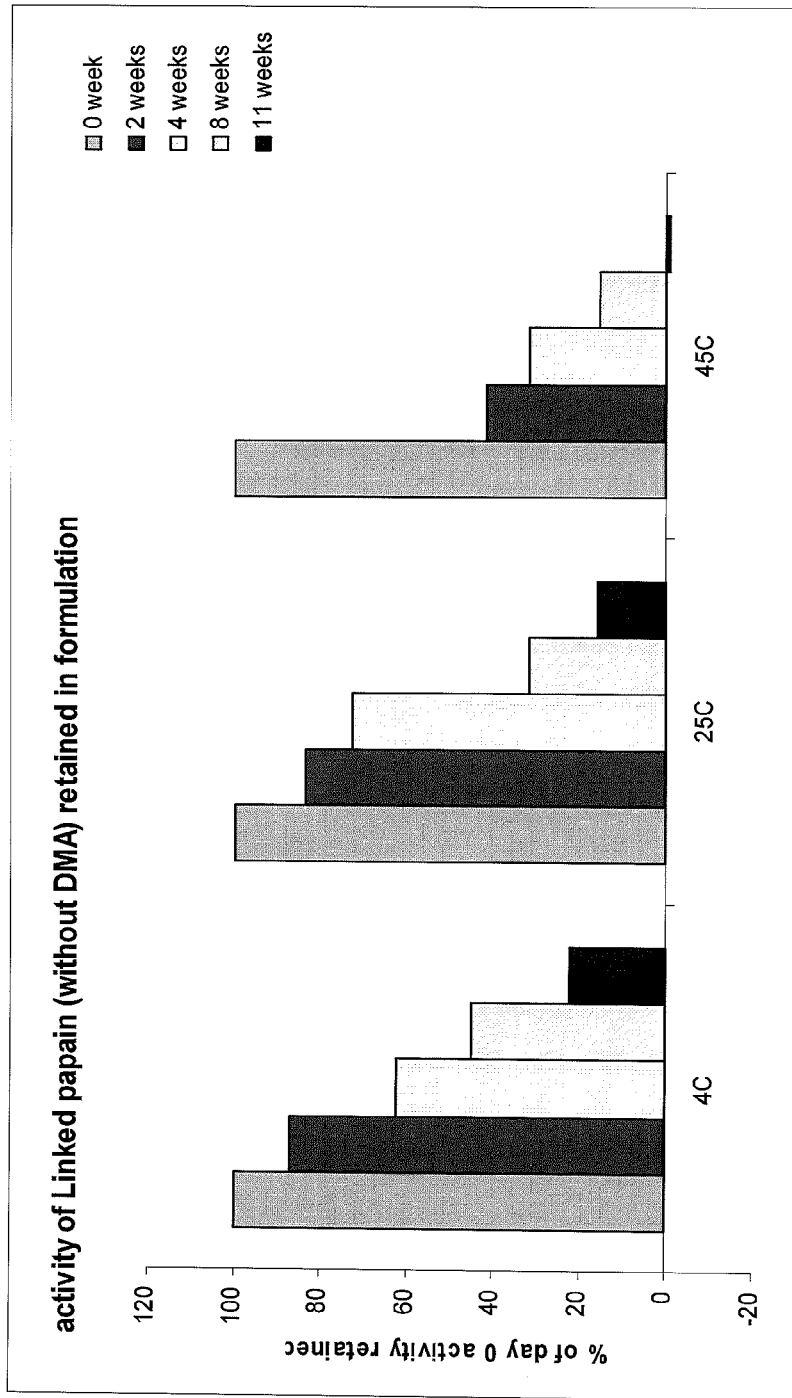
FIG. 18 is a chart which illustrates activity of linked papain (without DMA) retained in formulation.
Figure 19:
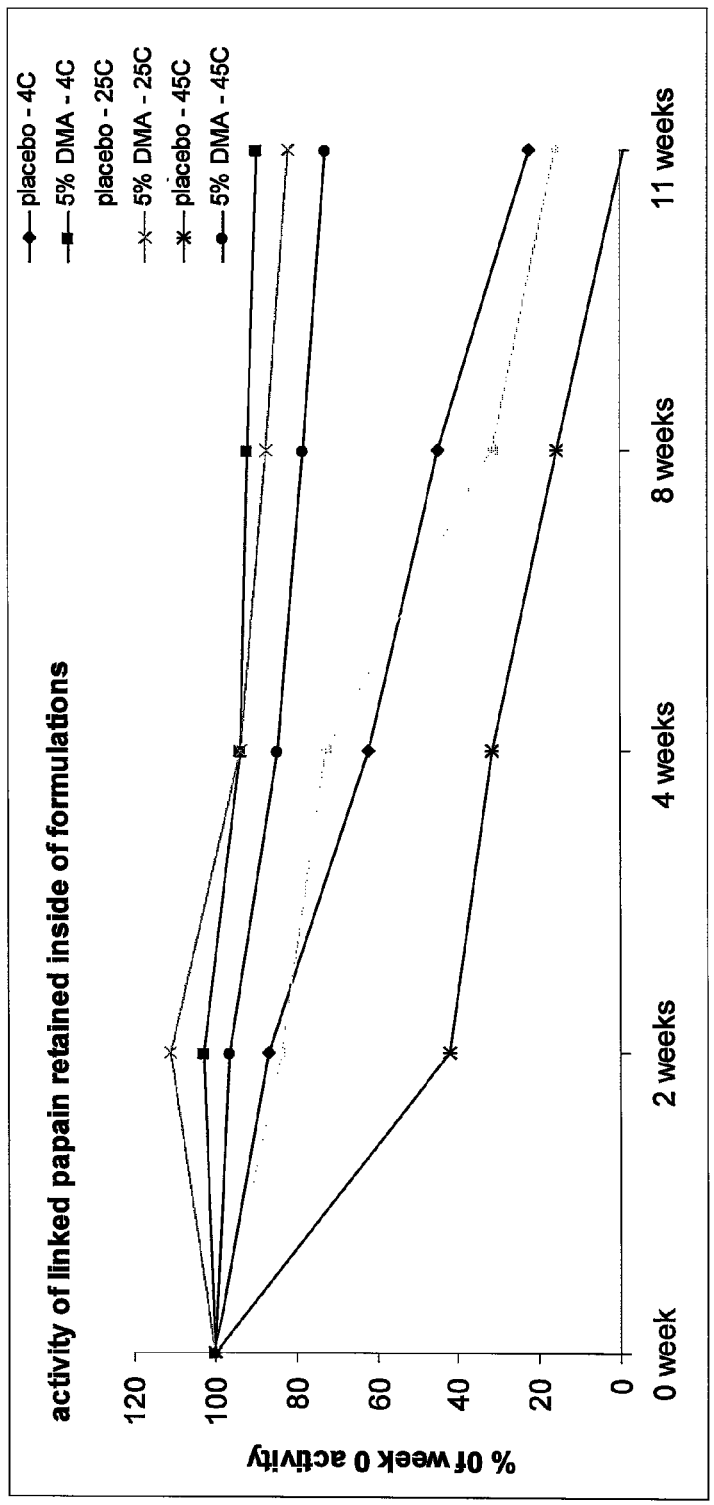
FIG. 19 is a graph illustrating the activity of linked papain retained inside of formulations

As can be gleaned from the above data table and FIGS. 17-19, crosslinking of immobilized papain with 5% DMA significantly improved the stability of the immobilized papain product over a variety of temperatures over a 12 week period in comparison to the control samples which did not contain any DMA.

Figure 20:
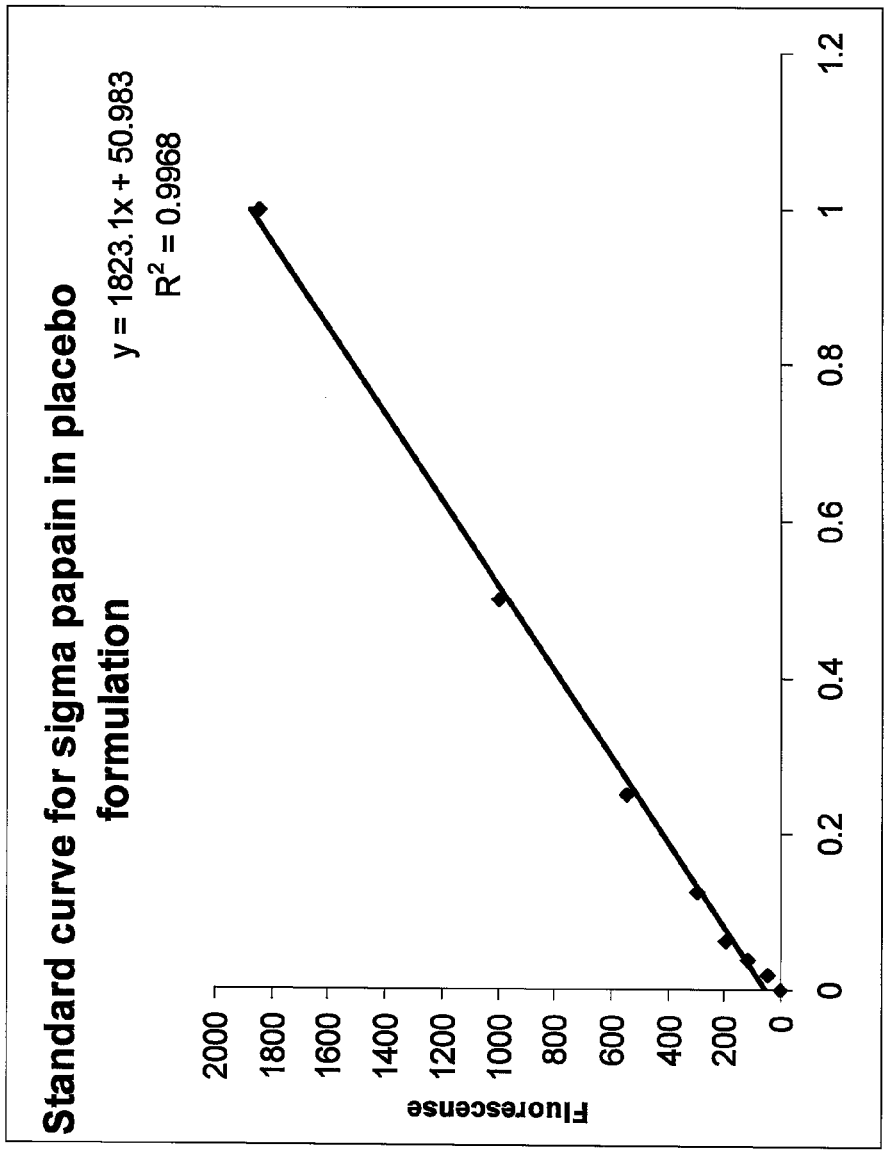
FIG. 20 is a standard curve for sigma papain in placebo formulation.

Furthermore, as set forth in the above data tables, papain activity in the experimental sample and the control were determined based upon fluorescence change per unit sample of the immobilized papain. A standard curve for Sigma papain the in placebo formulation as shown in FIG. 20 was developed for assistance in quantitating the activity of immobilized 1% papain cross-linked with 5% DMA in accordance with the present embodiment. As noted above, an EnzChek® protease assay kit (E-6639) was used to obtain the standard curve and the fluorescence change per unit sample of the experimental sample of linked papain with DMA in accordance with the present exemplary embodiment and the control sample without DMA.

Examples 6-8

The following represent nonlimiting examples of formulations that can be prepared using one or more stabilized proteases. A wide variety of similar formulations are known in the art into which one or more stabilized proteases can readily be incorporated at various concentrations.

Example 6

An exemplary elastic cream gel has, for example, the composition shown in the table below:

| PHASE | % | SUPPLIER | RAW MATERIAL | INCI NOMENCLATURE |
|---|---|---|---|---|
| A | 63.300 | Local | Deionized Water | Water |
| A | 0.050 | Local | Disodium EDTA | Disodium EDTA |
| A | 1.100 | Clariant | Aristoflex AVC/USA | Ammonium Acryloyldimethyltaurate/VP Copolymer |
| A | 0.150 | Clariant | Aristoflex HMB | Ammonium Acryloyldimethyltaurate/Beheneth-25 Methacrylate Crosspolymer |
| A | 3.000 | Local | Butylene Glycol | Butylene Glycol |
| A | 2.000 | Local | Glycerin | Glycerin |
| B | 15.000 | Momentive | Velvesil DM | Dimethicone and Cetearyl Dimethicone Crosspolymer |
| B | 3.000 | Dow Corning | Dow Corning 1413 | Dimethicone |
| C | 1.200 | Seppic | Simulgel NS | Hydroxyethyl Acrylate/Sodium Acryloyldimethyl Taurate Copolymer and Squalane and Polysorbate 60 |
| D | 3.000 | BASF | Stabilized papain of the present invention | |
| D | 1.000 | BASF | Germazide PSB | Phenoxyethanol, Chlorphenesin, Benzoic Acid, Butylene Glycol, Sorbic Acid |
| E | 2.000 | Alzo | CUPL PIC | PPG-2 Isoceteth-20 Acetate |
| E | 2.000 | Firmenich, Inc. | Hedione | Methyldihydrojasmonate |
| F | 0.100 | BASF | Cloisonne Red 424C | Mica and Titanium Dioxide and Carmine |
| F | 0.100 | BASF | Timica Silver Sparkle 5500 | Mica and Titanium Dioxide |
| F | 3.000 | Local | Water | Water |

In a main vessel, combine Phase A. Homo-mix and sweep-mix until powder is hydrated and batch is uniform. When Phase A is uniform, add phase B to main vessel while homo-mixing. Mix until uniform. Add phase C to main vessel while homo-mixing. Mix until uniform. Add phase D to main vessel while homo-mixing. Mix until uniform. Warm phase E ingredients to 150 to 40° C. until melted. Premix Phase E and add to main vessel while homo-mixing. Premix Phase F. Mix until all pearls are suspended and there are no clumps. Continue mixing during addition. Add Phase F to main vessel while homo-mixing. Turn off homo-mixer after addition and sweep-mix until uniform.

Example 7

An exemplary lotion has, for example, the composition shown in the table below

| PHASE | % | SUPPLIER | RAW MATERIAL | INCI NOMENCLATURE |
|-------|------|----------|--------------|-------------------|
| A | 85.50 | Local | Deionized Water | Water |
| A | 0.050 | Local | Disodium EDTA | Disodium EDTA |
| A | 3.0 | Local | 1,3 Butylene Glycol | Butylene Glycol |
| A | 1.0 | Clariant | Aristoflex AVC/USA | Ammonium Acryloyldimethyltaurate/VP Copolymer |
| B | 8.0 | Inolex | Lexol GT 865 | Caprylic/Capric Triglyceride |
| B | 0.25 | Arlacel 165V | Croda | Glyceryl Stearate and PEG-100 Stearate |
| C | 3.0 | | Stabilized papain of the present invention | |
| D | 1.2 | BASF | Germazide PSB | Phenoxyethanol and Chlorphenesin and Benzoic Acid and Butylene Glycol and Sorbic Acid |
| F | 3.000 | Local | Water | Water |

Mix phase A until homogenous while heating to 65-70° C. In separate vessel, premix phase B. Heat to 70-75° C. or until homogenous. When both phases A and B are at desired temperature, add phase B to phase A and homomix until uniform. When Phase AB is uniform, begin cooling add Phase C at 35-30° C. and mix under prop mixer until uniform. Add pre-mixed Phase D to Phase ABC under homomixer. Mix until uniform.

Example 8

In this embodiment, the stability of linked papain at various temperatures for up to 12 weeks in an O/W formulation. The results were obtained by a papain activity assay using an Invitrogen EnzChek assay kit after suspending the formulation in 0.1% Triton X-100, n=3.

Figure 21:
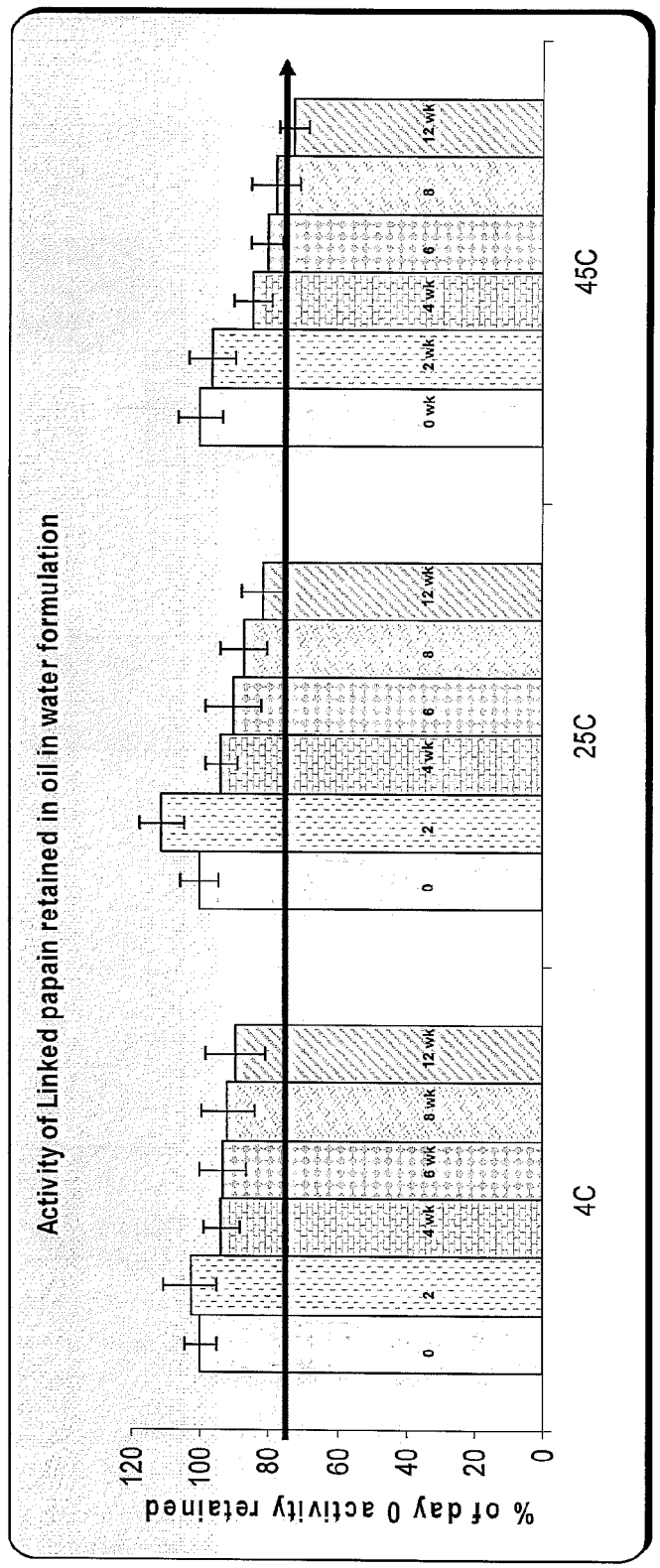
FIG. 21 is a chart which illustrates the activity of linked papain retained in an oil and water formulation.

As shown in FIG. 21, the linked papain product is further stabilized by an oil in water formulation. About 75% activity is retained after 12 weeks at 45 C. Formulation was found stable at all temperatures tested. These results indicate that when crosslinked papain products are included in an oil and water formulation that this product is even further stabilized.

Having described the exemplary embodiments of the present invention, it is further noted that it is readily apparent to those of reasonable skill in the art that various modifications may be made without departing from the spirit and scope of the invention which is defined by the metes and bounds of the appended claims.

The invention claimed is:

1. A stabilized protease product comprising a protease wherein the protease has been immobilized to a carbomer by reacting a portion of the primary amines of the protease with the carboxyl groups of the carbomer and wherein a portion of the remaining primary amines of the protease have been crosslinked via an amine reactive crosslinking reagent, wherein the crosslinking is performed by 1% to 5% by weight of the amine reactive crosslinking reagent and the amine reactive crosslinking reagent is selected from the group consisting of Dimethyl adipimidate (DMA), Bis(Sulfosuccinimidyl) suberate (BS3), Dimethyl Suberimidate (DMS), Dimethyl pimelimidate (DMP) and Disuccinimidyl suberate (DSS).

2. The stabilized protease of claim 1 wherein the stabilized protease further comprises a physical stabilizer.

3. The stabilized protease of claim 2 wherein the physical stabilizer is a sugar or sugar polymer.

4. The stabilized protease of claim 3 wherein the stabilized protease comprises between 0.1% and 5% of the physical stabilizer.

5. The stabilized protease of claim 3 wherein the sugar or sugar polymer is selected from the group consisting of sodium alginate, trehalose, mannitol, glycerol, xanthan gum, sucrose and sorbitol.

6. The stabilized protease of claim 5 wherein the physical stabilizer is sodium alginate.

7. The stabilized protease of claim 1 wherein the protease is selected from the group consisting of papain, ficin, bromelain, and actinidin.

8. The stabilized protease of claim 7 wherein the protease is papain.

9. The stabilized protease of claim 7 comprising between 0.1% and 5% of the protease.

10. The stabilized protease of claim 1 wherein the protease is papain and the amine reactive crosslinking reagent is DMA.

11. The stabilized protease product of claim 1 further comprising a preservative system.

12. The stabilized protease product of claim 11 wherein the preservative system comprises phenoxyethanol and benzoic acid.

13. The stabilized protease product according to claim 11 wherein the preservative system comprises diocide.

14. A method of forming a stabilized protease product comprising: immobilizing a protease to a carbomer by reacting a portion of the primary amines of the protease with the carboxyl groups of the carbomer; and performing a crosslinking reaction on the immobilized protease via an amine reactive crosslinking reagent, wherein the crosslinking reaction is performed by 1% to 5% by weight of the amine reactive crosslinking reagent, and the amine reactive crosslinking agent is selected from the group consisting of Dimethyl adipimidate (DMA), Bis(Sulfosuccinimidyl) suberate (BS3), Dimethyl Suberimidate (DMS), Dimethyl pimelimidate (DMP) and Disuccinimidyl suberate (DSS).

15. The method of claim 14, wherein the immobilization reaction is carried out using the reagents carbodiimide 1-ethyl-3(3-dimethyl aminopropyl)carbodiimide hydrochloride and N-hydroxysulfosuccinimide.

16. The method claim 14 wherein the amine reactive crosslinking reagent for performing the crosslinking reaction is DMA.

17. The method of claim 14, further comprising adding a physical stabilizer after performing the crosslinking reaction.

18. The method of claim 17 wherein the physical stabilizer is sodium alginate.

19. The method of claim 14, wherein the protease is papain and the amine reactive crosslinking reagent is DMA.

20. A method of treating dry, aged or damaged skin comprising application to the skin of a cosmetic composition comprising one or more stabilized protease products of claim 1.

21. A method of wound or burn debridement comprising topical application of a composition comprising one or more stabilized protease products of claim 1.

* * * * *